(12) United States Patent
Marubashi et al.

(10) Patent No.: US 11,311,053 B2
(45) Date of Patent: Apr. 26, 2022

(54) POWER SUPPLY UNIT FOR AEROSOL INHALER

(71) Applicant: Japan Tobacco Inc., Tokyo (JP)

(72) Inventors: Keiji Marubashi, Tokyo (JP); Hajime Fujita, Tokyo (JP)

(73) Assignee: JAPAN TOBACCO INC., Tokyo (JP)

(*) Notice: Subject to any disclaimer, the term of this patent is extended or adjusted under 35 U.S.C. 154(b) by 0 days.

(21) Appl. No.: 17/191,717

(22) Filed: Mar. 4, 2021

(65) Prior Publication Data

US 2021/0274853 A1    Sep. 9, 2021

(30) Foreign Application Priority Data

Mar. 5, 2020 (JP) .............................. JP2020-038192

(51) Int. Cl.
*A24F 13/00* (2006.01)
*A24F 17/00* (2006.01)
(Continued)

(52) U.S. Cl.
CPC .............. *A24F 40/57* (2020.01); *A24F 40/10* (2020.01); *A24F 40/53* (2020.01); *A61M 11/042* (2014.02);
(Continued)

(58) Field of Classification Search
CPC .......... A24F 40/10; A24F 40/50; A24F 40/53; A24F 40/57; A61M 11/042; A61M 15/06; A61M 2205/8206; H02J 7/0063
See application file for complete search history.

(56) References Cited

U.S. PATENT DOCUMENTS 5,204,991 A * 4/1993 Law ................. H02J 7/007188
307/10.7
10,045,567 B2 * 8/2018 Monsees ................. A24F 40/42
(Continued)

FOREIGN PATENT DOCUMENTS

CN    208354611 U    1/2019
JP    61-18594 U    2/1986
(Continued)

OTHER PUBLICATIONS

Notice of Reasons for Refusal dated Jun. 2, 2020, received for JP Application 2020-038192, 8 pages including English Translation.
(Continued)

*Primary Examiner* — Abdullah A Riyami
*Assistant Examiner* — Thang H Nguyen
(74) *Attorney, Agent, or Firm* — Xsensus LLP

(57) ABSTRACT

A power supply unit for an aerosol inhaler, which includes a power supply configured to discharge electricity to a load that is configured to heat an aerosol generation source and has a correlation between temperature and electric resistance values, includes: a first element connected in series to the load and having a first electric resistance value; a second series circuit that includes a second element having a second electric resistance value, and a third element connected in series to the second element and having a third electric resistance value, the second series circuit being connected in parallel with a first series circuit including the load and the first element; and an operational amplifier connected to the first series circuit and the second series circuit. The first electric resistance value is less than an electric resistance value of the load.

27 Claims, 16 Drawing Sheets

(51) Int. Cl.
*A24F 25/00* (2006.01)
*A24F 40/57* (2020.01)
*A61M 11/04* (2006.01)
*A24F 40/53* (2020.01)
*A24F 40/10* (2020.01)
*A61M 15/06* (2006.01)
*H02J 7/00* (2006.01)

(52) U.S. Cl.
CPC ............ *A61M 15/06* (2013.01); *H02J 7/0063* (2013.01); *A61M 2205/8206* (2013.01)

(56) References Cited

U.S. PATENT DOCUMENTS

| | | | |
|---|---|---|---|
| 11,166,493 B2* | 11/2021 | Mizuguchi | A61M 11/042 |
| 2004/0168513 A1 | 9/2004 | Aoshima et al. | |
| 2017/0021696 A1* | 1/2017 | Nagasaka | B60H 1/2218 |
| 2017/0177768 A1* | 6/2017 | Tsai | H01M 10/4285 |
| 2019/0393707 A1* | 12/2019 | Hunter | H02J 7/0063 |
| 2020/0375259 A1 | 12/2020 | Mizuguchi et al. | |

FOREIGN PATENT DOCUMENTS

| | | |
|---|---|---|
| JP | 2004-212102 A | 7/2004 |
| JP | 2017-501805 A | 1/2017 |
| JP | 6613008 B1 | 11/2019 |
| WO | 2015/100361 A1 | 7/2015 |

OTHER PUBLICATIONS

European Search Report dated Jul. 29, 2021 in European Application No. 21160983.9.

* cited by examiner

THIRD EMBODIMENT

SIXTH EMBODIMENT

SEVENTH EMBODIMENT

EIGHTH EMBODIMENT

FIG. 15

| | CONNECTION POSITION OF LOAD | TERMINAL CONNECTED TO OPERATIONAL AMPLIFIER OF FIRST SERIES CIRCUIT | PSEUDO GND | CONSTRAINT CONDITION | METHOD FOR RELAXING CONSTRAINT CONDITION |
|---|---|---|---|---|---|
| FIRST EMBODIMENT | LOW POTENTIAL | NON-INVERSION | NO | $R_1 \leq \frac{R_2}{R_3} \cdot R_{HTR}$ | - |
| SECOND EMBODIMENT | LOW POTENTIAL | NON-INVERSION | YES | $R_1 \geq \frac{(V_{OUT} + V_{PSEUDO}) \cdot R_2 + V_{PSEUDO} \cdot R_3}{(V_{OUT} - V_{PSEUDO}) \cdot R_3 - V_{PSEUDO} \cdot R_2} \cdot R_{HTR}$ | - |
| THIRD EMBODIMENT | LOW POTENTIAL | INVERSION | NO | $R_1 \geq \frac{R_2}{R_3} \cdot R_{HTR}$ | $R_3 > R_2$ |
| FOURTH EMBODIMENT | LOW POTENTIAL | INVERSION | YES | $R_1 \geq \frac{(V_{OUT} - V_{PSEUDO}) \cdot R_2 + V_{PSEUDO} \cdot R_3}{(V_{OUT} + V_{PSEUDO}) \cdot R_3 - V_{PSEUDO} \cdot R_2} \cdot R_{HTR}$ | $R_3 > \frac{V_{OUT} + 2V_{PSEUDO}}{V_{OUT} - 2V_{PSEUDO}} \cdot R_2$ |
| FIFTH EMBODIMENT | HIGH POTENTIAL | NON-INVERSION | NO | $R_1 \geq \frac{R_3}{R_2} \cdot R_{HTR}$ | $R_3 < R_2$ |
| SIXTH EMBODIMENT | HIGH POTENTIAL | NON-INVERSION | YES | $R_1 \geq \frac{(V_{OUT} - V_{PSEUDO}) \cdot R_3 + V_{PSEUDO} \cdot R_2}{(V_{OUT} + V_{PSEUDO}) \cdot R_2 - V_{PSEUDO} \cdot R_3} \cdot R_{HTR}$ | $R_3 < \frac{V_{OUT} + 2V_{PSEUDO}}{V_{OUT} - 2V_{PSEUDO}} \cdot R_2$ |
| SEVENTH EMBODIMENT | HIGH POTENTIAL | INVERSION | NO | $R_1 \leq \frac{R_3}{R_2} \cdot R_{HTR}$ | - |
| EIGHTH EMBODIMENT | HIGH POTENTIAL | INVERSION | YES | $R_1 \leq \frac{(V_{OUT} - V_{PSEUDO}) \cdot R_3 + V_{PSEUDO} \cdot R_2}{(V_{OUT} + V_{PSEUDO}) \cdot R_2 + V_{PSEUDO} \cdot R_3} \cdot R_{HTR}$ | - |

FIRST MODIFICATION OF FIRST EMBODIMENT

SECOND MODIFICATION OF FIRST EMBODIMENT

US 11,311,053 B2

POWER SUPPLY UNIT FOR AEROSOL INHALER

CROSS-REFERENCE TO RELATED APPLICATION

This application is based on and claims priority under 35 USC 119 from Japanese Patent Application No. 2020-038192 filed on Mar. 5, 2020, the contents of which are incorporated herein by reference.

TECHNICAL FIELD

The present invention relates to a power supply unit for an aerosol inhaler.

BACKGROUND ART

JP-T-2017-501805 (hereinafter, referred to as Patent Literature 1) discloses a circuit that measures a resistance value of a heater in a device that generates an inhalable aerosol.

Since an aerosol inhaler is held by a user in a mouth thereof when used, temperature management of a heater used to generate aerosol is important. The temperature management of the heater is also important from the viewpoint of ensuring an amount of aerosol and a fragrance.

Meanwhile, it is also required to improve generation efficiency of the aerosol such that more aerosol can be generated. Although the measurement of the resistance value of the heater is disclosed in Patent Literature 1, a specific configuration thereof is not disclosed.

An object of the present invention is to provide a power supply unit for an aerosol inhaler capable of detecting a temperature of a load used to generate aerosol with high accuracy while improving the generation efficiency of the aerosol.

SUMMARY OF INVENTION

A power supply unit for an aerosol inhaler, which includes a power supply configured to discharge electricity to a load that is configured to heat an aerosol generation source and has a correlation between temperature and electric resistance values, includes: a first element connected in series to the load and having a first electric resistance value; a second series circuit that includes a second element having a second electric resistance value, and a third element connected in series to the second element and having a third electric resistance value, the second series circuit being connected in parallel with a first series circuit including the load and the first element; and an operational amplifier connected to the first series circuit and the second series circuit. The first electric resistance value is less than an electric resistance value of the load.

According to the present invention, the temperature of the load used to generate the aerosol can be detected with high accuracy while the generation efficiency of the aerosol is improved.

BRIEF DESCRIPTION OF DRAWINGS

Exemplary embodiment(s) of the present invention will be described in detail based on the following figures, wherein:

FIG. 15 summarizes the respective configurations of the first to eighth embodiments and constraint conditions for preventing occurrence of a lower limit clip;

DESCRIPTION OF EMBODIMENTS

Figure 1:
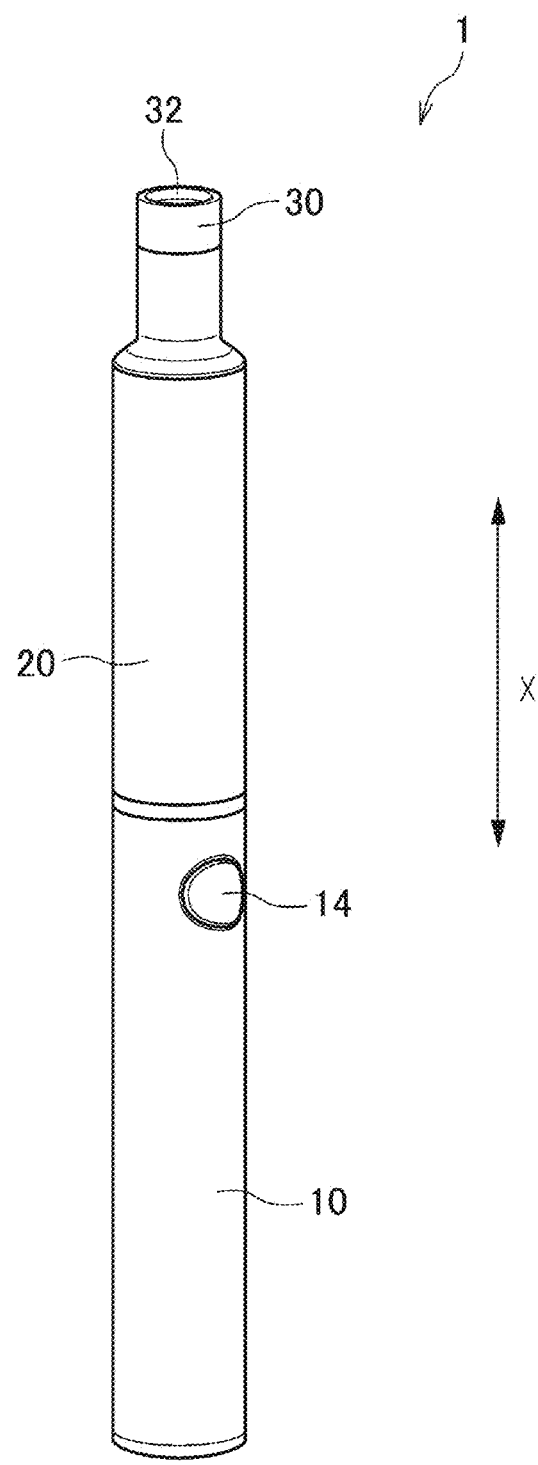
FIG. 1 is a perspective view of an aerosol inhaler equipped with a power supply unit of one embodiment of the present invention.

Hereinafter, a power supply unit for an aerosol inhaler according to an embodiment of the present invention will be described. First, the aerosol inhaler equipped with the power supply unit will be described with reference to FIGS. 1 and 2.

(Aerosol Inhaler)

An aerosol inhaler 1 is an instrument for inhaling a perfumed aerosol without burning, and has a rod shape extending along a predetermined direction (hereinafter referred to as a longitudinal direction X). In the aerosol inhaler 1, a power supply unit 10, a first cartridge 20, and a second cartridge 30 are provided in such an order along the longitudinal direction X. The first cartridge 20 can be attached to and detached from the power supply unit 10. The second cartridge 30 can be attached to and detached from the first cartridge 20. In other words, the first cartridge 20 and the second cartridge 30 are replaceable.

(Power Supply Unit)

As shown in FIGS. 3, 4, 5 and 6, the power supply unit 10 of the present embodiment accommodates, inside a cylindrical power supply unit case 11, a power supply 12, a charging IC 55A, a micro controller unit (MCU) 50, and various sensors, such as an intake sensor 15. The power supply 12 is a rechargeable secondary battery, an electric double layer capacitor or the like, and is preferably a lithium ion secondary battery. An electrolyte of the power supply 12 may include one of a gel electrolyte, an electrolytic solution, a solid electrolyte, an ionic liquid, or a combination thereof.

Figure 4:
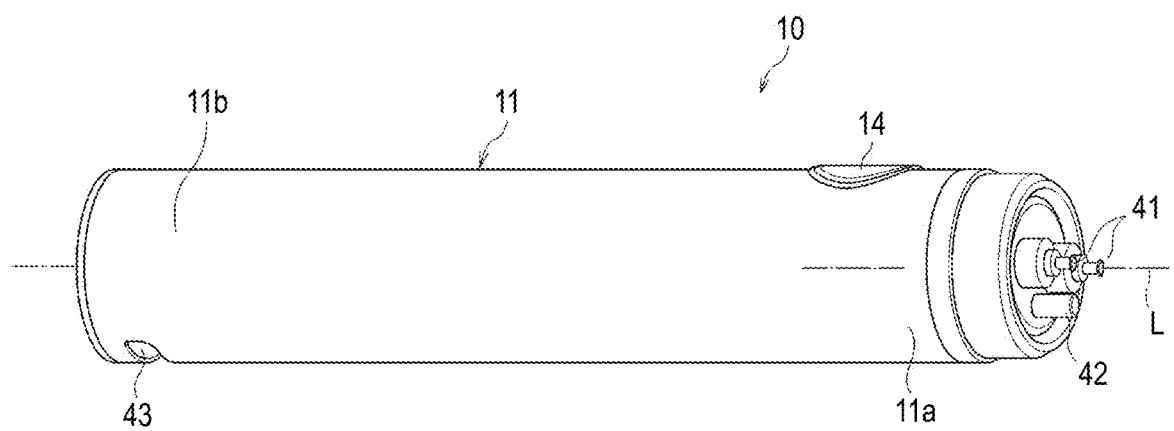
FIG. 4 is a perspective view of the power supply unit of the aerosol inhaler shown in FIG. 1.

As shown in FIG. 4, a discharge terminal 41 is provided on a top portion 11*a* located on one end side (side of the first cartridge 20) of the power supply unit case 11 in the longitudinal direction X. The discharge terminal 41 protrudes from an upper surface of the top portion 11*a* toward the first cartridge 20, and is configured to be electrically connectable to a load 21 of the first cartridge 20.

An air supply unit 42 configured to supply air to the load 21 of the first cartridge 20 is provided on the upper surface of the top portion 11*a* in the vicinity of the discharge terminal 41.

A charge terminal 43 that is electrically connectable to an external power supply (not shown) capable of charging the power supply 12 is provided on a bottom portion 11*b* located on the other end side (side opposite to the first cartridge 20) of the power supply unit case 11 in the longitudinal direction X. The charge terminal 43 is provided on a side surface of the bottom portion 11*b*, and is connectable with at least one of a USB (Universal Serial Bus) terminal, a micro USB terminal, and a Lightning (registered trademark) terminal, for example.

The charge terminal 43 may be a power receiving unit capable of receiving power transmitted from the external power supply in a non-contact manner. In such a case, the charge terminal 43 (power receiving unit) may include a power receiving coil. A method for transmitting power in a non-contact manner (wireless power transfer) may be an electromagnetic induction type or a magnetic resonance type. The charge terminal 43 may also be a power receiving unit capable of contactlessly receiving power transmitted from the external power supply. As another example, the charge terminal 43 may be connectable with at least one of a USB terminal, a micro USB terminal, and a Lightning terminal, and include the power receiving unit described above.

Figure 3:
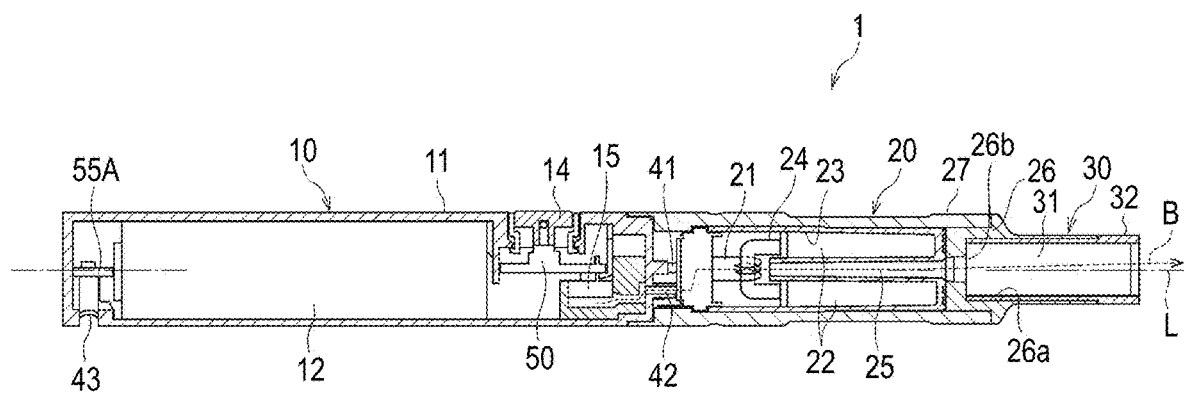
FIG. 3 is a cross-sectional view of the aerosol inhaler shown in FIG. 1.

An operation portion 14 that can be operated by a user is provided on the power supply unit case 11 so as to face a side opposite to the charge terminal 43 on a side surface of the top unit 11*a*. More specifically, the operation portion 14 and the charge terminal 43 have a point-symmetric relationship with respect to an intersection of a straight line connecting the operation portion 14 and the charge terminal 43 and a center line of the power supply unit 10 in the longitudinal direction X. The operation portion 14 includes a button type switch, a touch panel, or the like. As shown in FIG. 3, the intake sensor 15 that detects a puff operation is provided in the vicinity of the operation portion 14.

The charging IC 55A is arranged in proximity to the charge terminal 43, and controls charging of power input from the charge terminal 43 to the power supply 12. The charging IC 55A may also be arranged in the vicinity of the MCU 50.

Figure 5:
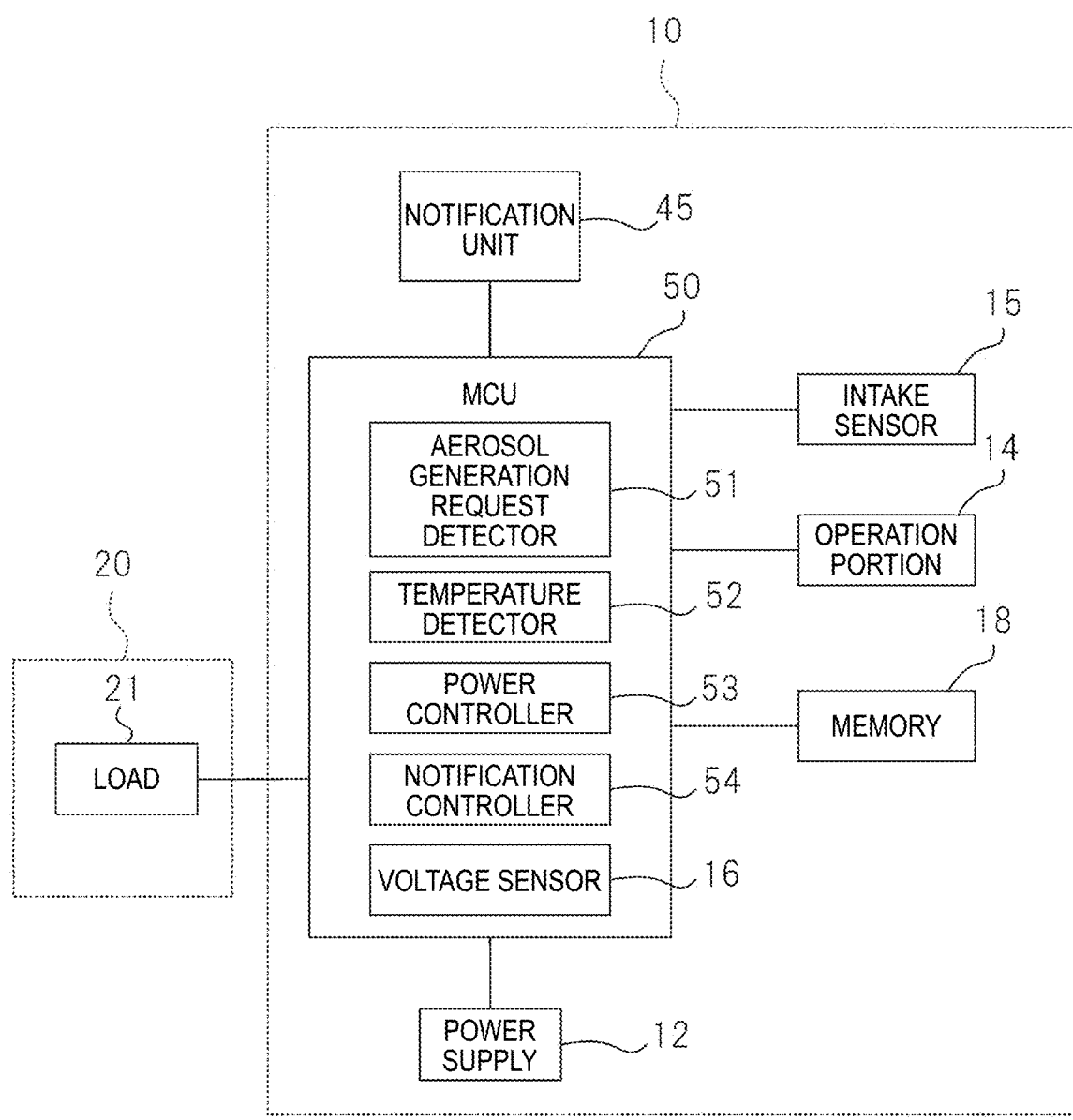
FIG. 5 is a block diagram showing a configuration of a main part the power supply unit of the aerosol inhaler shown in FIG. 1.

As shown in FIG. 5, the MCU 50 is connected to various sensor devices (such as the intake sensor 15 that detects the puff (intake) operation), the operation portion 14, a notification unit 45 to be described below, and a memory 18 that stores the number of times of puff operations, a time of energization to the load 21 or the like so as to perform various types of control of the aerosol inhaler 1. The memory 18 may also be built in the MCU 50. Specifically, the MCU 50 mainly includes a processor 55 (see FIG. 7), which will be described below, and further includes storage media, such as a random access memory (RAM) necessary for operations of the processor 55 and a read only memory (ROM) that stores various types of information. More specifically, the processor in the present specification is an electric circuit in which circuit elements such as semiconductor elements are combined.

The MCU 50 includes a voltage sensor 16 that measures a power supply voltage of the power supply 12. The voltage sensor 16 may include an operational amplifier 56 and an ADC 57, which will be described later below. In the MCU 50, an output signal of the voltage sensor 16 is input to the processor 55. Instead of the configuration of the present embodiment, the voltage sensor 16 may also be provided outside the MCU 50 and connected to the MCU 50.

The power supply unit case 11 is provided with an air intake port (not shown) configured therein to take in outside air. The air intake port may be provided around the operation portion 14, or may be provided around the charge terminal 43.

(First Cartridge)

As shown in FIG. 3, inside a cylindrical cartridge case 27, the first cartridge 20 includes a reservoir 23 that stores an aerosol source 22, the electric load 21 that atomizes the aerosol source 22, a wick 24 that draws the aerosol source from the reservoir 23 to the load 21, an aerosol flow path 25 through which aerosol generated by the atomization of the aerosol source 22 flows toward the second cartridge 30, and an end cap 26 that accommodates a part of the second cartridge 30.

The reservoir 23 is partitioned to surround a periphery of the aerosol flow path 25, and stores the aerosol source 22. A porous body, such as a resin web or cotton, may be accommodated in the reservoir 23, and the aerosol source 22 may be impregnated in the porous body. The reservoir 23 may only store the aerosol source 22 without accommodating the porous body such as the resin web or cotton. The aerosol source 22 includes a liquid such as glycerin, propylene glycol or water.

The wick 24 is a liquid holding member that draws the aerosol source 22 from the reservoir 23 to the load 21 by utilizing a capillary phenomenon. The wick 24 is made of, for example, glass fiber or porous ceramic.

The load 21 atomizes the aerosol source 22 by heating the aerosol source 22 by power supplied from the power supply 12 via the discharge terminal 41 without burning. The load 21 is formed of an electric heating wire (coil) wound at a predetermined pitch.

The load 21 may be any element that can perform atomization by heating the aerosol source 22 to generate the aerosol. The load 21 is, for example, a heat generating element. Examples of the heat generating element include a heat generating resistor, a ceramic heater, an induction heating type heater, and the like. Hereinafter, an electric resistance value of the load 21 will be referred to as an electric resistance value $R_{HTR}$.

A load whose temperature and electric resistance values are correlated is used as the load 21. For example, a load having a positive temperature coefficient (PTC) characteristic, which causes the electric resistance value to increase as the temperature increases, is used as the load 21. The PTC characteristic is also referred to as a positive resistance temperature coefficient characteristic.

The aerosol flow path 25 is downstream of the load 21 and is provided on a center line L of the power supply unit 10. The end cap 26 includes: a cartridge accommodating portion 26a that accommodates a part of the second cartridge 30, and a communication path 26b that connects the aerosol flow path 25 and the cartridge accommodating portion 26a.

(Second Cartridge)

The second cartridge 30 stores a perfume source 31. The second cartridge 30 is detachably accommodated in the cartridge accommodating portion 26a provided in the end cap 26 of the first cartridge 20. An end portion, which is located on a side opposite to the side of the first cartridge 20, of the second cartridge 30 serves as a user inhale port 32. The inhale port 32 is not limited to be formed integrally with the second cartridge 30, and may also be detachable from the second cartridge 30. By forming the inhale port 32 separately from the power supply unit 10 and the first cartridge 20 in this way, the inhale port 32 can be kept hygienic.

The aerosol generated by atomizing the aerosol source 22 by the load 21 is passed through the perfume source 31 in the second cartridge 30, so that the aerosol is imparted with a perfume. Chopped tobacco or a molded body obtained by molding a tobacco raw material into particles can be used as a raw material piece that forms the perfume source 31. The perfume source 31 may also be formed of a plant other than tobacco (for example, mint, Chinese herb, or herb). The perfume source 31 may also be provided with a fragrance such as menthol.

According to the aerosol inhaler 1 of the present embodiment, a perfumed aerosol can be generated by the aerosol source 22, the perfume source 31, and the load 21. That is, the aerosol source 22 and the perfume source 31 constitute an aerosol generation source that generates the aerosol.

The aerosol generation source of the aerosol inhaler 1 is a portion that is replaced and used by the user. As this portion, for example, one first cartridge 20 and one or a plurality of (for example, five) second cartridges 30 are provided to the user as a set.

In addition to a configuration in which the aerosol source 22 and the perfume source 31 are separated from each other, a configuration in which the aerosol source 22 and the perfume source 31 are integrally formed, a configuration in which the perfume source 31 is omitted and substances that can be included in the perfume source 31 are added to the aerosol source 22, or a configuration in which a medicine or the like is added to the aerosol source 22 instead of the perfume source 31 may also be employed as the configuration of the aerosol generation source used in the aerosol inhaler 1.

In a case where the aerosol inhaler 1 includes the aerosol generation source in which the aerosol source 22 and the perfume source 31 are integrally formed, for example, one or a plurality of (for example, 20) aerosol generation sources are provided as a set to the user.

In a case where the aerosol inhaler 1 only includes the aerosol source 22 as the aerosol generation source, for example, one or a plurality of (for example, 20) aerosol generation sources are provided as a set to the user.

According to the aerosol inhaler 1 configured in this way, as indicated by arrow B in FIG. 3, air flowing in from the intake port (not shown) provided in the power supply unit case 11 passes through the vicinity of the load 21 of the first cartridge 20 from the air supply unit 42. The load 21 atomizes the aerosol source 22 drawn by the wick 24 from the reservoir 23. The aerosol generated by atomization flows through the aerosol flow path 25 together with the air flowing in from the intake port, and is supplied to the second cartridge 30 via the communication path 26b. The aerosol supplied to the second cartridge 30 passes through the perfume source 31 so as to be perfumed, and is then supplied to the inhale port 32.

The aerosol inhaler 1 is provided with the notification unit 45 that notifies various types of information (see FIG. 5). The notification unit 45 may include a light emitting element, a vibrating element, or a sound output element. The notification unit 45 may also be a combination of two or more elements among the light emitting element, the vibrating element, and the sound output element. The notification unit 45 may be provided in any one of the power supply unit 10, the first cartridge 20, and the second cartridge 30, and is preferably provided in the power supply unit 10. For example, a configuration in which a periphery of the operation portion 14 is translucent and emits light by a light emitting element such as an LED is employed.

First Embodiment of Electric Circuit

Figure 2:
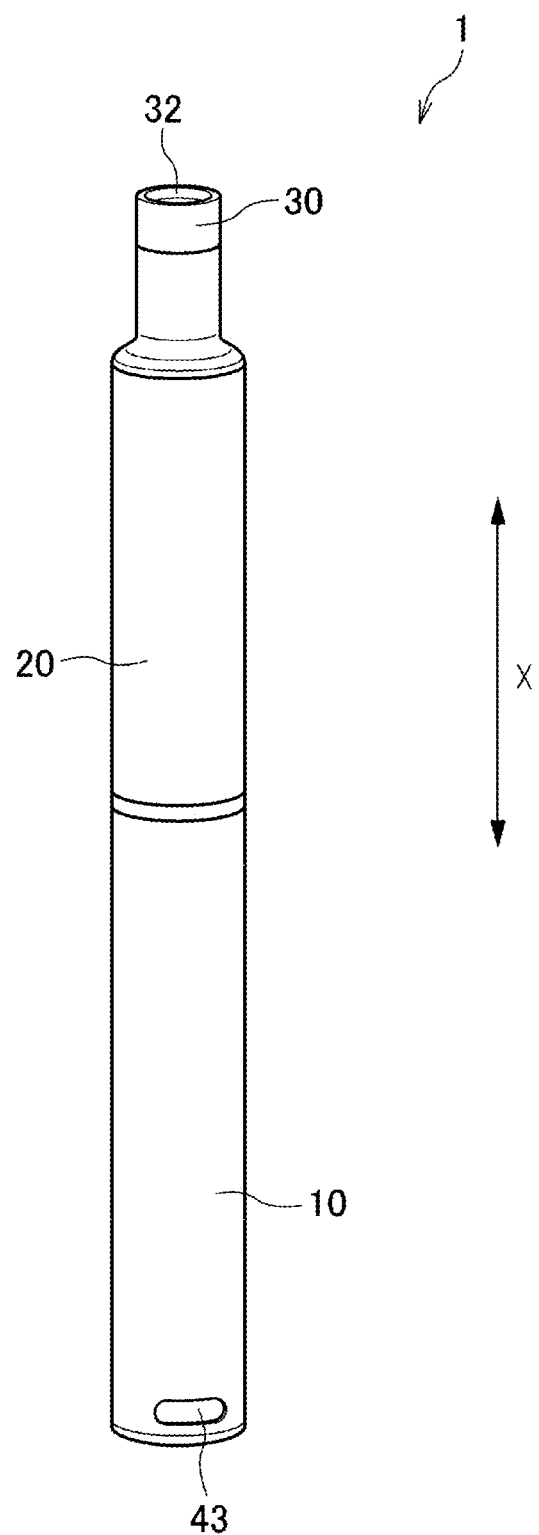
FIG. 2 is another perspective view of the aerosol inhaler shown in FIG. 1.
Figure 6:
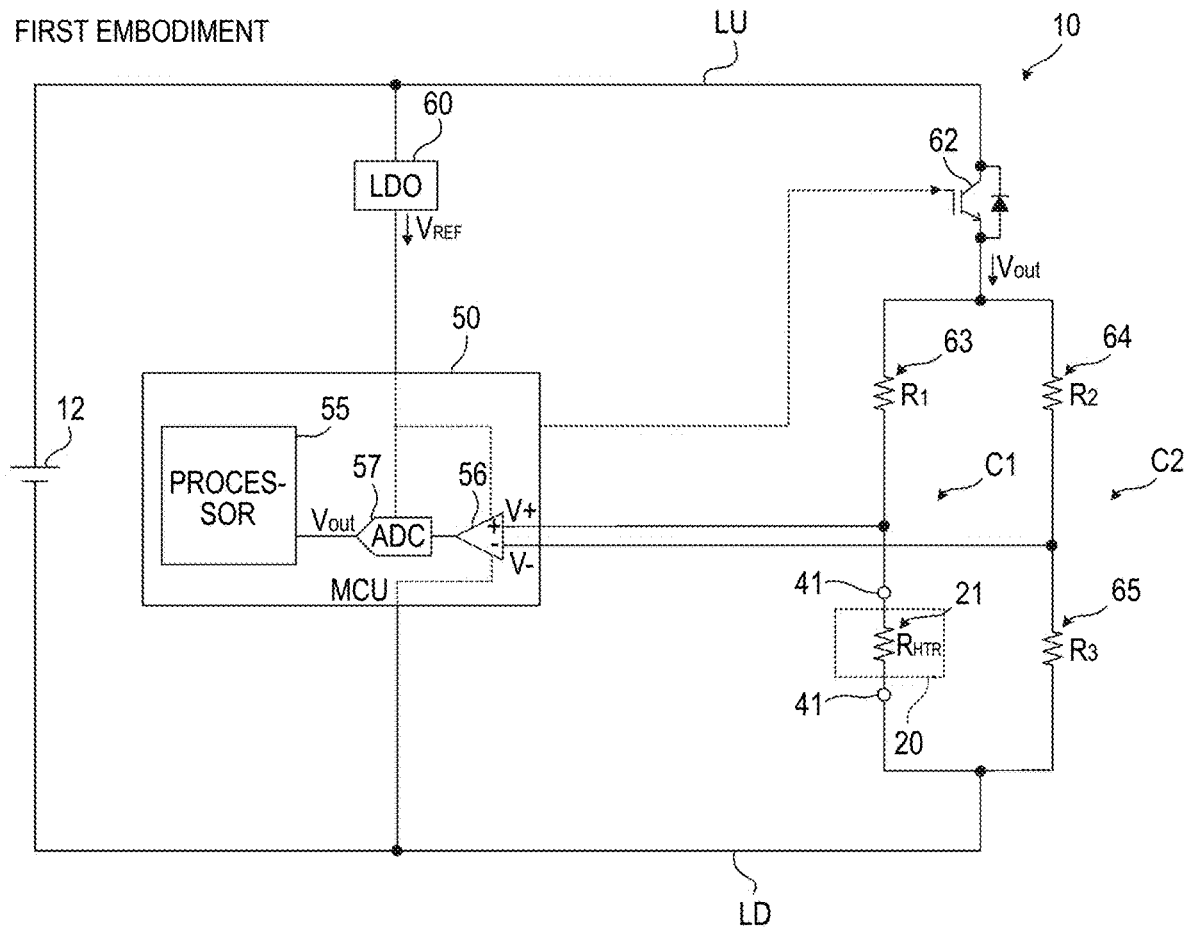
FIG. 6 is a schematic diagram showing a first embodiment of a circuit configuration of the power supply unit of the aerosol inhaler shown in FIG. 1.

FIG. 6 is a schematic diagram showing a first embodiment of a circuit configuration of the power supply unit of the aerosol inhaler shown in FIG. 1. As shown in FIG. 6, the power supply unit 10 includes, as main circuit configurations, the power supply 12, the discharge terminal 41 where the first cartridge 20 including the load 21 is detachably attached, the MCU 50, a low drop out (LDO) regulator 60, a switch 62, a first element 63 having a first electric resistance value $R_1$, a second element 64 having a second electric resistance value $R_2$ and a third element 65 having a third electric resistance value $R_3$.

Each of the first element 63, the second element 64, and the third element 65 is an element having an electric resistance value, for example, a resistor, a diode, or a transistor. In the example of FIG. 6, the first element 63, the second element 64, and the third element 65 are resistors.

The switch 62 is a switching element such as a transistor that switches between blocking and conduction of a wiring path. In the example of FIG. 6, the switch 62 is a normally-off type insulated gate bipolar transistor (IGBT) that is turned on (conducted) upon receiving a high-level turn-on command signal supplied from the MCU 50 and is turned off (blocked) upon receiving a low-level turn-off command signal supplied from the MCU 50. A field effect transistor (FET) may be used as the switch 62 instead of the IGBT.

The LDO regulator 60 and the MCU 50 are connected to the power supply 12. The LDO regulator 60 steps down and outputs a voltage from the power supply 12. An output voltage of the LDO regulator 60 (hereinafter, referred to as a reference voltage $V_{REF}$) is applied to the MCU 50 as an operation voltage of the MCU 50. For example, the LDO regulator 60 steps down a voltage of 4.2 V from the power supply 12 to 3.7 V and outputs the voltage. Among a main positive bus LU and a main negative bus LD, the main positive bus LU is a line on a high potential side, and the main negative bus line LD is a line on a low potential side. In the example of FIG. 6, the main positive bus LU is a line having a highest potential in the electric circuit of the power supply unit 10. In the example of FIG. 6, the main negative bus LD is a line having a lowest potential (specifically, 0 V) in the electric circuit of the power supply unit 10.

The MCU 50 is connected to the LDO regulator 60 and the main negative bus LD that is connected to a negative electrode of the power supply 12. The MCU 50 is also connected to the switch 62, and controls on and off of the switch 62. Hereinafter, a voltage applied to a bridge circuit including a first series circuit C1 and a second series circuit C2 in a state where the switch 62 is turned on will be referred to as a voltage $V_{OUT}$. The voltage $V_{OUT}$ may be the same as the reference voltage $V_{REF}$.

In a state where the first cartridge 20 is attached to the power supply unit 10, the first element 63 and the load 21 are connected in series to form the first series circuit C1. The second element 64 and the third element 65 are connected in series to form the second series circuit C2.

The first series circuit C1 and the second series circuit C2 are connected in parallel between the main positive bus LU and the main negative bus LD. Specifically, a collector of the switch 62 is connected to the main positive bus LU, and the first element 63 and the second element 64 are connected in parallel to an emitter of the switch 62. The load 21 and the third element 65 are connected in parallel to the main negative bus LD. The load 21 is connected to the first element 63, and the third element 65 is connected to the second element 64. The first series circuit C1 has a configuration in which the first element 63 is connected to the high potential side of the load 21.

The first series circuit C1 is connected to the MCU 50. Specifically, in the first series circuit C1, a connection node between the first element 63 and the load 21 is connected to the MCU 50.

The second series circuit C2 is connected to the MCU 50. Specifically, in the second series circuit C2, a connection node between the second element 64 and the third element 65 is connected to the MCU 50.

The MCU 50 includes the operational amplifier 56, the analog-to-digital converter (ADC) 57, and the processor 55. In all embodiments, at least one of the operational amplifier 56 and the ADC 57 may be provided outside the MCU 50.

The operational amplifier 56 includes a non-inversion input terminal (+) and an inversion input terminal (−), amplifies a differential input voltage obtained by subtracting a potential $V_-$ input to the inversion input terminal from a potential $V_+$ input to the non-inversion input terminal by a predetermined amplification factor A and outputs the amplified differential input voltage. The differential input voltage changes when the electric resistance value of the load 21 changes in accordance with the temperature thereof. Similarly, an output signal of the operational amplifier 56 changes when the electric resistance value of the load 21 changes in accordance with the temperature thereof.

The operational amplifier 56 includes a pair of power supply terminals. As an example, the reference voltage $V_{REF}$ is supplied to the power supply terminal on the high potential side (hereinafter, referred to as a positive power supply terminal). The power supply terminal on the low potential side (hereinafter, referred to as a negative power supply terminal) is connected to the main negative bus LD. In the following description, unless otherwise specified, the operational amplifier 56 is an input-output rail-to-rail type operational amplifier. When the power supply terminal of the operational amplifier 56 is connected in this way, an upper limit value of a range of the differential input voltage that can be amplified by the operational amplifier 56 (hereinafter referred to as an amplification range) is a potential connected to the positive power supply terminal (reference voltage $V_{REF}$ as an example), and a lower limit value of the amplification range is a potential connected to the negative power supply terminal (0V). Accordingly, when the differential input voltage is below 0 V, the differential input voltage is clipped to 0 V (such a phenomenon is referred to as a lower limit clip). Similarly, when the differential input voltage is above the reference voltage $V_{REF}$, the differential input voltage is clipped to the reference voltage $V_{REF}$ (such a phenomenon is referred to as an upper limit clip). If the voltage (reference voltage $V_{REF}$) supplied to the positive power supply terminal of the operational amplifier 56 coincides with the voltage $V_{OUT}$, occurrence of the upper limit clip can be prevented. Therefore, it is particularly important to devise prevention of occurrence of the lower limit clip.

When the operational amplifier 56 is not the input-output rail-to-rail type operational amplifier, the upper limit value of the amplification range is lower than that of the input-output rail-to-rail type operational amplifier, and the lower limit value of the amplification range is higher than that of the input-output rail-to-rail type operational amplifier. In other words, the amplification range of the operational amplifier 56 which is not the input-output rail-to-rail type operational amplifier is narrower than the amplification range of the input-output rail-to-rail type operational amplifier 56. Therefore, it should be noted that when the operational amplifier 56 that is not the input-output rail-to-rail type operational amplifier is used, the upper limit clip and the lower limit clip occur easily.

The first series circuit C1 is connected to the non-inversion input terminal of the operational amplifier 56. Specifically, the non-inversion input terminal of the operational amplifier 56 is connected to a point between the first element 63 and the load 21 in the first series circuit C1. The second series circuit C2 is connected to the inversion input terminal of the operational amplifier 56. Specifically, the inversion input terminal of the operational amplifier 56 is connected to a point between the second element 64 and the third element 65 in the second series circuit C2.

The ADC 57 converts the output signal of the operational amplifier 56 into a digital signal and outputs the digital signal. The ADC 57 is operated with the reference voltage $V_{REF}$.

As shown in FIG. 5, the MCU 50 includes, as functional blocks implemented by the processor 55 executing programs stored in the ROM, an aerosol generation request detector 51, a temperature detector 52, a power controller 53, and a notification controller 54.

The aerosol generation request detector 51 detects an aerosol generation request based on an output result of the intake sensor 15. The intake sensor 15 is configured to output a value of a pressure (internal pressure) change in the power supply unit 10 caused by the user's inhale through the inhale port 32. The intake sensor 15 is, for example, a pressure sensor that outputs an output value (for example, a voltage value or a current value) corresponding to an internal pressure that changes in accordance with a flow rate of air inhaled from the intake port (not shown) toward the inhale port 32 (that is, the puff operation of the user). The intake sensor 15 may include a condenser microphone or the like. The intake sensor 15 may also output an analog value, or may output a digital value converted from the analog value.

The temperature detector 52 detects the temperature of the load 21 based on the output signal of the operational amplifier 56 shown in FIG. 6. When the switch 62 is turned on, currents flow in the first series circuit C1 and the second series circuit C2 respectively, and the temperature detector 52 detects the temperature of the load 21 based on the output signal of the operational amplifier 56 at this time.

The notification controller 54 controls the notification unit 45 to notify various types of information. For example, the notification controller 54 controls the notification unit 45 to notify replacement timing of the second cartridge 30 in response to detection of the replacement timing of the second cartridge 30. The notification controller 54 detects and notifies the replacement timing of the second cartridge 30 based on the cumulative number of times of puff operations or cumulative time of energization to the load 21 stored in the memory 18. The notification controller 54 is not limited to only notify the replacement timing of the second cartridge 30, and may also notify replacement timing of the first cartridge 20, replacement timing of the power supply 12, charging timing of the power supply 12, and the like.

In a state where one unused second cartridge 30 is set, when the puff operation is performed a predetermined number of times or when the cumulative time of energization to the load 21 reaches a predetermined value (for example, 120 seconds) due to the puff operation, the notification controller 54 determines that the second cartridge 30 has been used up (that is, a remaining amount is zero or empty), and notifies the replacement timing of the second cartridge 30.

When it is determined that all the second cartridges 30 included in the above one set have been used up, the notification controller 54 may determine that one first cartridge 20 included in the one set has been used up (that is, the remaining amount is zero or empty) and notify the replacement timing of the first cartridge 20.

When the aerosol generation request detector 51 detects the aerosol generation request, the power controller 53 turns on or off the switch 62 so as to control discharge of the power supply 12 performed via the discharge terminal 41. By turning on the switch 62, the power controller 53 causes a current to flow through the load 21 to discharge electricity to the load 21. The currents flow through the first series circuit C1 and the second series circuit C2 both in the case where electricity is discharged to the load 21 and in the case where the temperature of the load 21 is detected as described above. That is, the MCU 50 is configured to acquire the temperature of the load 21 based on the output of the operational amplifier 56 while supplying power to the bridge circuit such that the load 21 generates the aerosol from the aerosol generation source.

Hereinafter, a combined resistance value of the first series circuit C1 ($R_1+R_{HTR}$) is referred to as $R_L$, and the combined resistance value ($R_2+R_3$) of the second series circuit C2 is referred to as $R_R$. An electric resistance value of the entire bridge circuit including the first series circuit C1 and the second series circuit C2 ($R_R \cdot R_L/(R_R+R_L)$) is referred to as $R_{BRIDGE}$.

Reference Example of Electric Circuit

Figure 7:
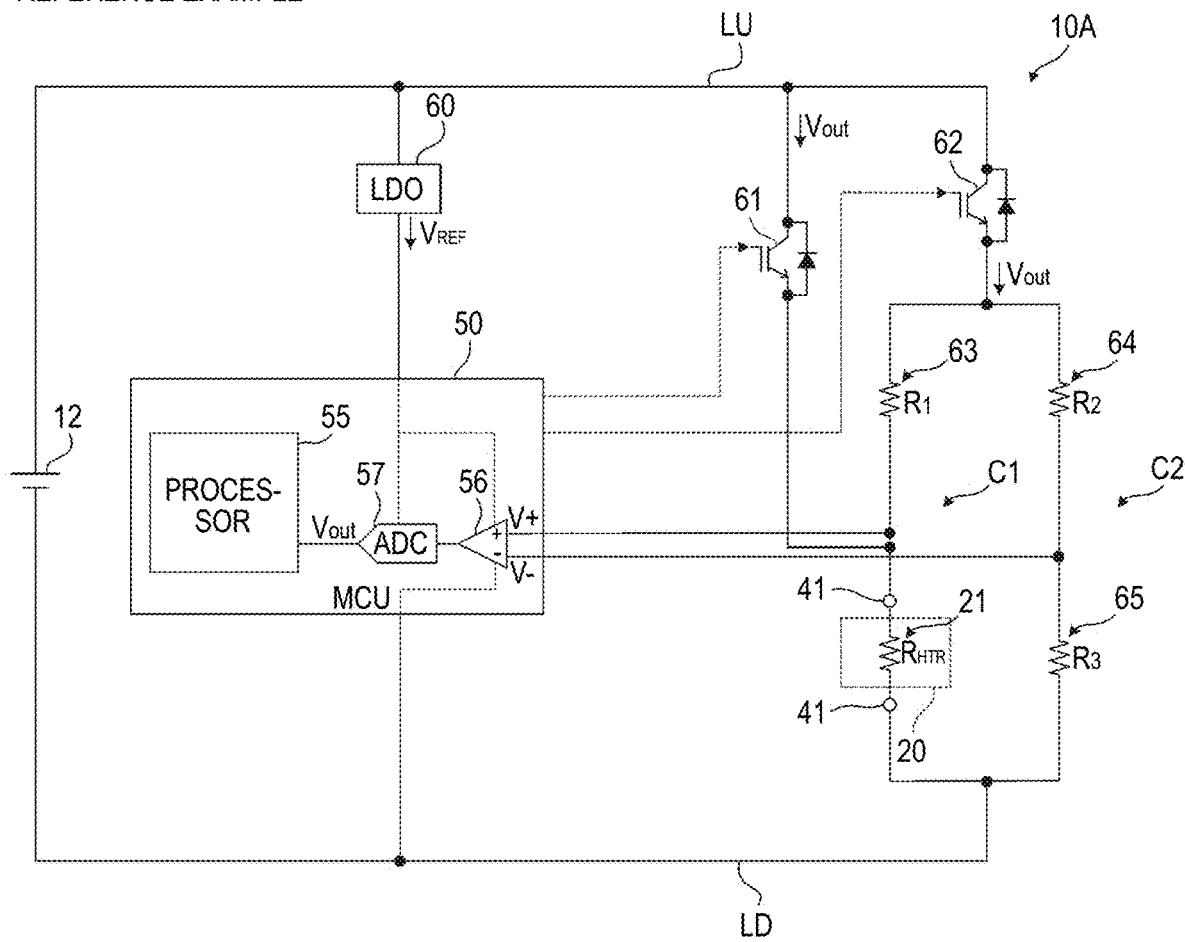
FIG. 7 is a schematic diagram showing a reference example of the circuit configuration of the power supply unit of the aerosol inhaler shown in FIG. 1.

FIG. 7 is a schematic diagram showing a reference example of the circuit configuration of the power supply unit of the aerosol inhaler shown in FIG. 1. The circuit shown in FIG. 7 is the same as the circuit configuration of FIG. 6 except that a switch 61 is added. The switch 61 is a normally-off type IGBT that is turned on upon receiving the high-level turn-on command signal supplied from the MCU 50 and is turned off upon receiving the low-level turn-off command signal supplied from the MCU 50. An emitter of the switch 61 is connected to a point between a connection node between the first series circuit C1 and the operational amplifier 56 and the load 21. A collector of the switch 61 is connected to the main positive bus LU.

An operation of the electric circuit shown in FIG. 7 will be described. Upon detecting the aerosol generation request, the processor 55 of the MCU 50 sends a turn-on command to the switch 61, and sends a turn-off command to the switch 62. In response to such commands, the switch 61 is turned on, and the switch 62 is turned off. For example, by minimizing the electric resistance value $R_{HTR}$ of the load 21 in the bridge circuit, a large current can flow through the load 21 while a current flowing through the first element 63, the second element 64, and the third element 65 can become zero or substantially zero in a state where the switch 61 is turned on while the switch 62 is turned off. As a result, the load 21 is heated to generate the aerosol. A voltage applied to the bridge circuit including the first series circuit C1 and the second series circuit C2 in a state where the switch 61 is turned off while the switch 62 is turned on is the same as the voltage $V_{OUT}$ described above. A voltage applied to the load 21 in the state where the switch 61 is turned on while the switch 62 is turned off is also the same as the voltage $V_{OUT}$.

After a lapse of a predetermined time from a start of the heating of the load 21, the processor 55 sends the turn-off command to the switch 61, and sends the turn-on command to the switch 62. When the switch 61 is turned off and the switch 62 is turned on in response to such commands, currents flow to the first series circuit C1 and the second series circuit C2. A differential input voltage is amplified by the operational amplifier 56, subjected to digital conversion performed by the ADC 57, and input to the processor 55. The processor 55 detects the temperature of the load 21 based on an input signal from the ADC 57.

After detecting the temperature of the load 21, the processor 55 sends the turn-on command to the switch 61, and sends the turn-off command to the switch 62 to start generation of the aerosol again. By repeating the above operations, the temperature of the load 21 is detected at high frequency during the generation of the aerosol in response to the aerosol generation request.

In the reference example shown in FIG. 7, since power can be substantially supplied only to the load 21 during the generation of the aerosol, generation efficiency of the aerosol can be improved. In the first embodiment shown in FIG. 6, power is supplied to the first series circuit C1 and the second series circuit C2 during the generation of the aerosol. Therefore, in order to improve the generation efficiency of the aerosol, it is desirable that the power supplied to the load 21 is equal to the power supplied to the load 21 during the generation of the aerosol in the reference example shown in FIG. 7. Hereinafter, conditions that can improve the generation efficiency of the aerosol in the first embodiment shown in FIG. 6 will be described.

In the first embodiment shown in FIG. 6, the power supplied to the load 21 during the generation of the aerosol (in the state where the switch 62 is turned on) is referred to as $P_{BRIDGE}$. In the reference example of FIG. 7, the power supplied to the load 21 during the generation of the aerosol (in the state where the switch 62 is turned off while the switch 61 is turned on) is referred to as $P_{BYPASS}$. $P_{BRIDGE}$ and $P_{BYPASS}$ are represented by the following Formulas (1) and (2). IL in Formula (1) indicates a current flowing through the load 21 when the switch 62 is turned on in the first embodiment shown in FIG. 6. $V_{HTR}$ in Formula (1) indicates a voltage applied to the load 21 when the switch 62 is turned on in the first embodiment shown in FIG. 6.

$$P_{BRIDGE} = I_L \cdot V_{HTR} = \left(\frac{V_{OUT}}{R_{BRIDGE}} \cdot \frac{R_R}{R_L + R_R}\right) \cdot \left(V_{OUT} \cdot \frac{R_{HTR}}{R_1 + R_{HTR}}\right) \quad (1)$$

$$P_{BYPASS} = \frac{V_{OUT}^2}{R_{HTR}} \quad (2)$$

A difference between $P_{BRIDGE}$ and $P_{BYPASS}$ is represented by the following Formula (3). From Formula (3), it can be seen that the first electric resistance value $R_1$ of the first element 63 should be reduced so as to bring $P_{BRIDGE}$ closer to $P_{BYPASS}$. Therefore, in the electric circuit shown in FIG. 6, the first electric resistance value $R_1$ of the first element 63 is the lowest among electric resistance values of elements constituting the bridge circuit. The electric resistance value $R_{HTR}$ of the load 21 is mainly in a range of 0.8 to 1.5Ω. Therefore, the first electric resistance value $R_1$ is preferably set to a value lower than 0.8Ω. In order to improve the generation efficiency of the aerosol, it is preferable to set the combined resistance value $R_L$ to be lower than the combined resistance value $R_R$ such that more power is supplied to the load 21.

$$P_{BYPASS} - P_{BRIDGE} = \frac{V_{OUT}^2}{R_{HTR}} - \left(\frac{V_{OUT}}{R_{BRIDGE}} \cdot \frac{R_R}{R_L + R_R}\right). \quad (3)$$

$$= \frac{\left(V_{OUT} \cdot \frac{R_{HTR}}{R_1 + R_{HTR}}\right)}{}$$

$$= \left(\frac{1}{R_{HTR}} - \frac{R_L + R_R}{R_L \cdot R_R} \cdot \frac{R_R}{R_L + R_R} \cdot \frac{R_{HTR}}{R_1 + R_{HTR}}\right) \cdot V_{OUT}^2$$

$$= \left(\frac{1}{R_{HTR}} - \frac{1}{R_L} \cdot \frac{R_{HTR}}{R_1 + R_{HTR}}\right) \cdot V_{OUT}^2$$

$$= \left\{\frac{1}{R_{HTR}} - \frac{R_{HTR}}{(R_1 + R_{HTR})^2}\right\} \cdot V_{OUT}^2$$

Meanwhile, in the first embodiment shown in FIG. 6, the differential input voltage of the operational amplifier 56 needs to be equal to or higher than a potential of the negative power supply terminal of the operational amplifier 56 (=0 V) so as to secure detection accuracy of the temperature of the load 21 (so that the lower limit clip does not occur). In the first embodiment shown in FIG. 6, the differential input voltage of the operational amplifier 56 is represented by the following Formula (4).

$$V_+ - V_- = \frac{R_{HTR}}{R_L} \cdot V_{OUT} - \frac{R_3}{R_R} \cdot V_{OUT} \quad (4)$$

In order to prevent occurrence of the lower limit clip in the operational amplifier 56 of the first embodiment, it is necessary to satisfy a condition that Formula (4) is equal to or higher than 0. That is, in the first embodiment, it is preferable to determine the electric resistance values of the elements of the bridge circuit in such a manner that the following Formula (5) is satisfied.

$$V_+ - V_- \geq 0 \rightarrow \frac{R_{HTR}}{R_L} \cdot V_{OUT} \geq \frac{R_3}{R_R} \cdot V_{OUT} \rightarrow R_{HTR} \cdot R_R \geq R_3 \cdot R_L \rightarrow \quad (5)$$

$$R_{HTR} \cdot (R_2 + R_3) \geq R_3 \cdot (R_1 + R_{HTR}) \rightarrow R_1 \leq \frac{R_2}{R_3} \cdot R_{HTR}$$

Second Embodiment of Electric Circuit

Figure 8:
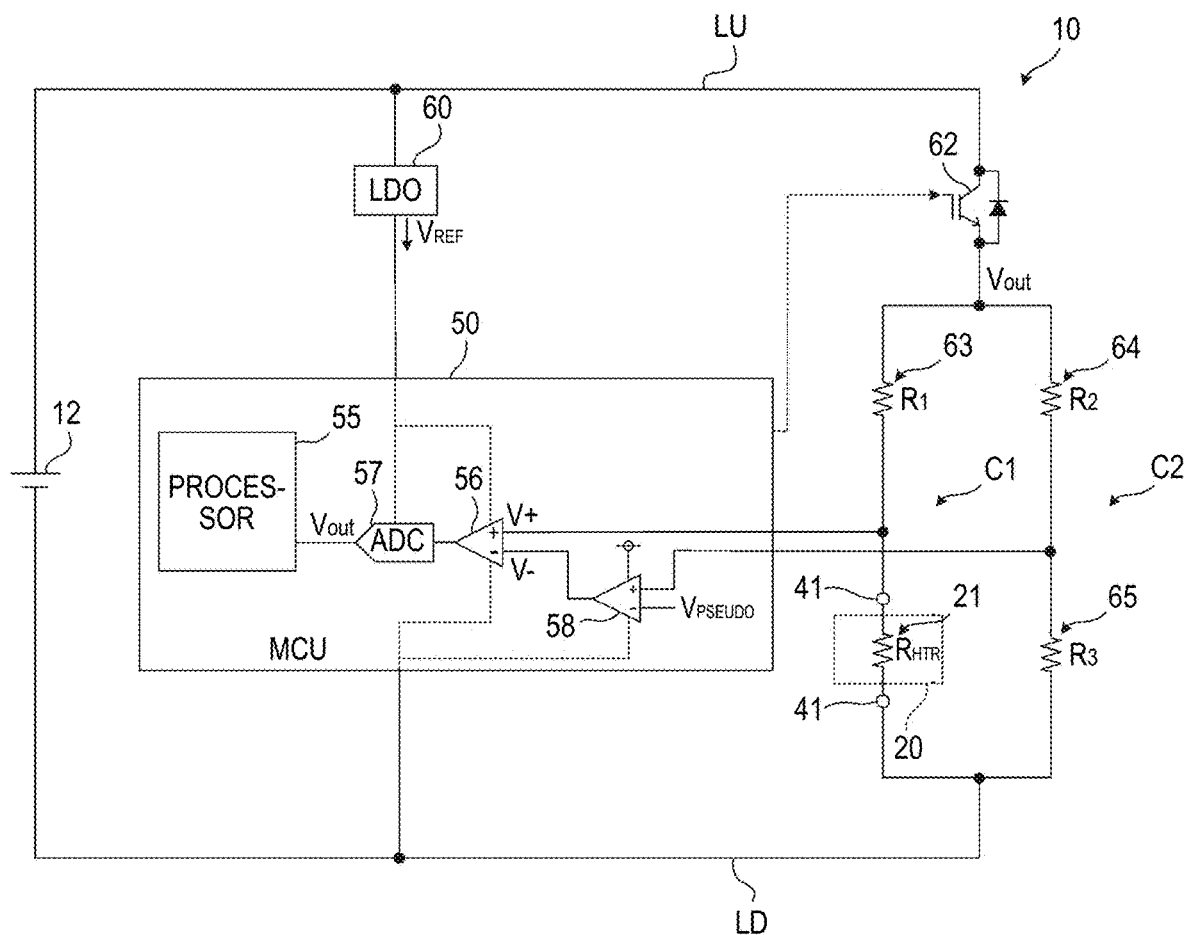
FIG. 8 is a schematic diagram showing a second embodiment of the circuit configuration of the power supply unit of the aerosol inhaler shown in FIG. 1.

FIG. 8 is a schematic diagram showing a second embodiment of the circuit configuration of the power supply unit of the aerosol inhaler shown in FIG. 1. The circuit shown in FIG. 8 is the same as the circuit configuration of FIG. 6 except that an operational amplifier 58 having an amplification factor of 1 is added in the MCU 50.

A non-inversion input terminal of the operational amplifier 58 is connected to a point between the second element 64 and the third element 65 in the second series circuit C2. An inversion input terminal of the operational amplifier 58 is connected to a circuit that supplies a default potential $V_{PSEUDO}$. An output terminal of the operational amplifier 58 is connected to the inversion input terminal of the operational amplifier 56. For example, the reference voltage $V_{REF}$ is supplied to a positive power supply terminal of the operational amplifier 58. A negative power supply terminal of the operational amplifier 58 is connected to, for example, the main negative bus LD.

The operational amplifier 58 functions to lower the lower limit value of the amplification range of the operational amplifier 56 (that is, the potential of the negative power supply terminal) in a pseudo manner. When the operational amplifier 58 is added to the first embodiment shown in FIG. 6, the differential input voltage of the operational amplifier 56 is lifted by $V_{PSEUDO}$. As a result, even when a potential of the connection node between the first element 63 and the load 21 is lower than a potential of the connection node between the second element 64 and the third element 65, it is possible to prevent the occurrence of the lower limit clip, and it is possible to detect the temperature of the load 21 with high accuracy.

In order to prevent occurrence of the lower limit clip in the operational amplifier 56 of the second embodiment, it is necessary to satisfy a condition that the differential input voltage of the operational amplifier 56 is equal to or higher than 0. That is, in the second embodiment, it is preferable to determine the electric resistance values of the elements of the bridge circuit in such a manner that the following Formula (6) is satisfied. If $V_{PSEUDO}$ is set to 0 in Formula (6), Formula (6) is the same as Formula (5).

$$V_+ - (V_- - V_{PSEUDO}) \geq 0 \rightarrow \quad (6)$$

$$\frac{R_{HTR}}{R_L} \cdot V_{OUT} \geq \frac{R_3}{R_R} \cdot V_{OUT} - V_{PSEUDO} \rightarrow \frac{R_{HTR}}{R_L} \geq \frac{R_3}{R_R} - \frac{V_{PSEUDO}}{V_{OUT}} \rightarrow$$

$$R_{HTR} \cdot R_R \geq R_3 \cdot R_L - \frac{V_{PSEUDO}}{V_{OUT}} \cdot R_L \cdot R_R \rightarrow R_{HTR} \cdot (R_2 + R_3) \geq$$

$$R_3 \cdot (R_1 + R_{HTR}) - \frac{V_{PSEUDO}}{V_{OUT}} \cdot (R_2 + R_3) \cdot (R_1 + R_{HTR}) \rightarrow$$

$$R_{HTR} \cdot (R_2 + R_3) \geq \left\{R_3 - \frac{V_{PSEUDO}}{V_{OUT}} \cdot (R_2 + R_3)\right\} \cdot R_1 +$$

$$R_3 \cdot R_{HTR} - \frac{V_{PSEUDO}}{V_{OUT}} \cdot (R_2 + R_3) \cdot R_{HTR} \rightarrow$$

$$R_{HTR} \cdot R_2 \geq \left\{R_3 - \frac{V_{PSEUDO}}{V_{OUT}} \cdot (R_2 + R_3)\right\} \cdot R_1 -$$

$$\frac{V_{PSEUDO}}{V_{OUT}} \cdot (R_2 + R_3) \cdot R_{HTR} \rightarrow$$

$$R_{HTR} \cdot R_2 + \frac{V_{PSEUDO}}{V_{OUT}} \cdot (R_2 + R_3) \cdot R_{HTR} \geq$$

$$\left(\frac{V_{OUT} - V_{PSEUDO}}{V_{OUT}} \cdot R_3 - \frac{V_{PSEUDO}}{V_{OUT}} \cdot R_2\right) \cdot R_1 \rightarrow$$

$$\left(\frac{V_{OUT} + V_{PSEUDO}}{V_{OUT}} \cdot R_2 + \frac{V_{PSEUDO}}{V_{OUT}} \cdot R_3\right) \cdot R_{HTR} \geq$$

$$\left(\frac{V_{OUT} - V_{PSEUDO}}{V_{OUT}} \cdot R_3 - \frac{V_{PSEUDO}}{V_{OUT}} \cdot R_2\right) \cdot R_1 \rightarrow$$

$$\{(V_{OUT} + V_{PSEUDO}) \cdot R_2 + V_{PSEUDO} \cdot R_3\} \cdot R_{HTR} \geq$$

-continued $$\{(V_{OUT} - V_{PSEUDO}) \cdot R_3 - V_{PSEUDO} \cdot R_2\} \cdot R_1 \rightarrow$$

$$R_1 \lesssim \frac{(V_{OUT} + V_{PSEUDO}) \cdot R_2 + V_{PSEUDO} \cdot R_3}{(V_{OUT} - V_{PSEUDO}) \cdot R_3 - V_{PSEUDO} \cdot R_2} \cdot R_{HTR}$$

Third Embodiment of Electric Circuit

Figure 9:
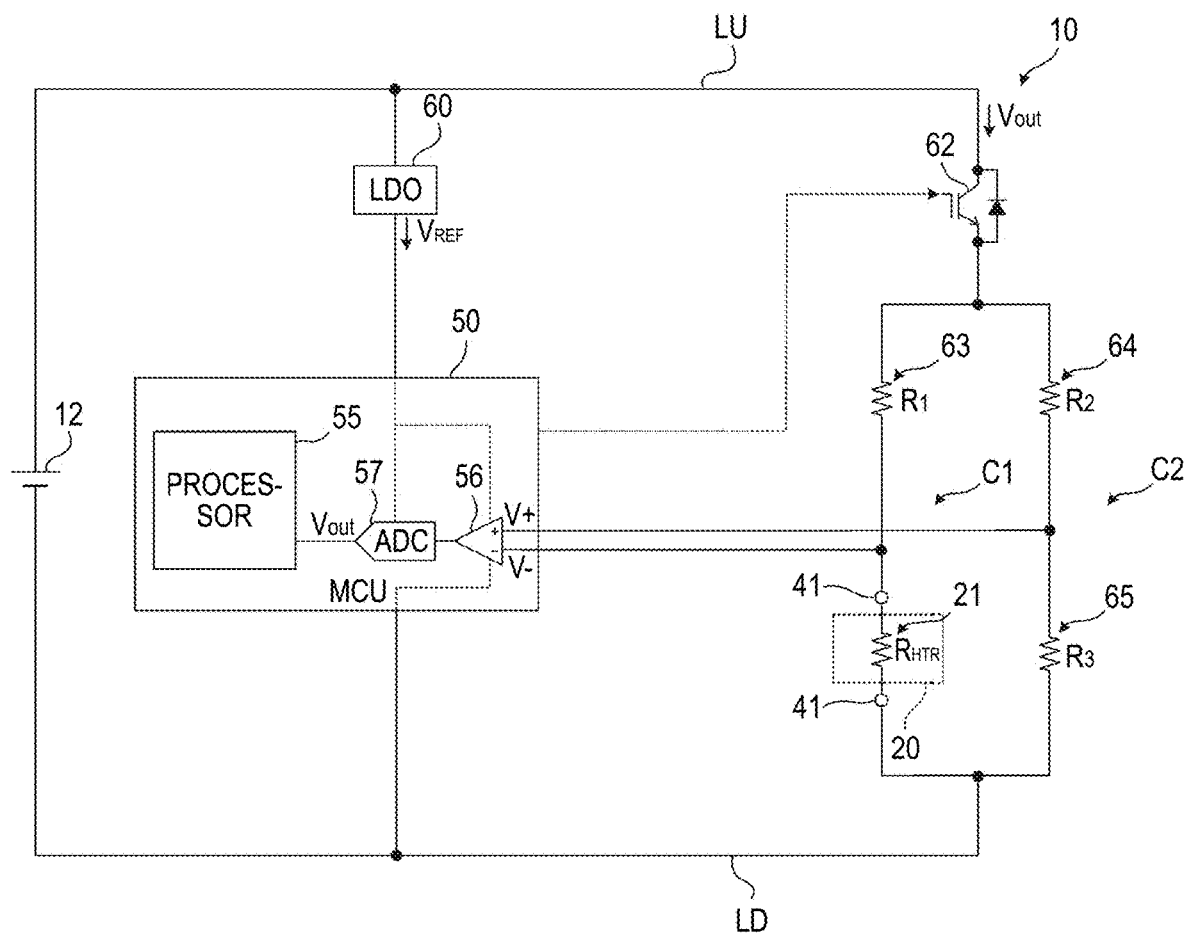
FIG. 9 is a schematic diagram showing a third embodiment of the circuit configuration of the power supply unit of the aerosol inhaler shown in FIG. 1.

FIG. 9 is a schematic diagram showing a third embodiment of the circuit configuration of the power supply unit of the aerosol inhaler shown in FIG. 1. The circuit shown in FIG. 9 is the same as the circuit configuration of FIG. 6 except that a connection relationship between the operational amplifier 56 and the bridge circuit is changed. In the circuit shown in FIG. 9, the inversion input terminal of the operational amplifier 56 is connected to the connection node between the first element 63 and the load 21. The non-inversion input terminal of the operational amplifier 56 is connected to the connection node between the second element 64 and the third element 65. In the third embodiment shown in FIG. 9, the differential input voltage of the operational amplifier 56 is represented by the following Formula (7).

$$V_+ - V_- = \frac{R_3}{R_R} \cdot V_{OUT} - \frac{R_{HTR}}{R_L} \cdot V_{OUT} \qquad (7)$$

In order to prevent occurrence of the lower limit clip in the operational amplifier 56 of the third embodiment, it is necessary to satisfy a condition that Formula (7) is equal to or higher than 0. That is, in the third embodiment, it is preferable to determine the electric resistance values of the elements of the bridge circuit in such a manner that the following Formula (8) is satisfied.

$$R_1 \gtrsim \frac{R_2}{R_3} \cdot R_{HTR} \qquad (8)$$

In the third embodiment, as can be seen from Formula (8), a lower limit of the first electric resistance value $R_1$ is restricted. As described above, in order to improve the generation efficiency of the aerosol, the first electric resistance value $R_1$ is preferably minimized. Therefore, in the third embodiment, the first electric resistance value $R_1$ can be minimized by setting the third electric resistance value $R_3$ to be higher than the second electric resistance value $R_2$.

Fourth Embodiment of Electric Circuit

Figure 10:
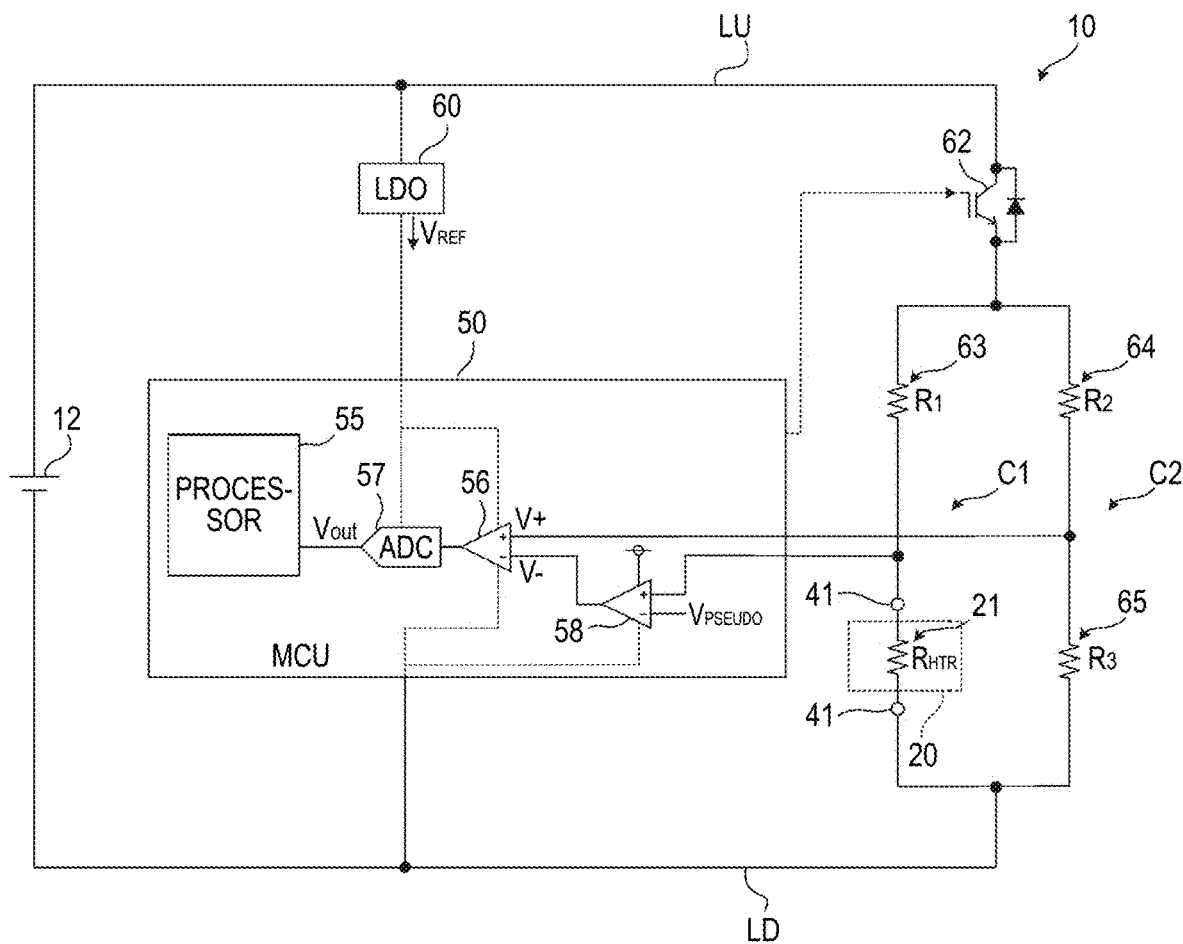
FIG. 10 is a schematic diagram showing a fourth embodiment of the circuit configuration of the power supply unit of the aerosol inhaler shown in FIG. 1.

FIG. 10 is a schematic diagram showing a fourth embodiment of the circuit configuration of the power supply unit of the aerosol inhaler shown in FIG. 1. The circuit shown in FIG. 10 is the same as the circuit configuration of FIG. 8 except that the non-inversion input terminal of the operational amplifier 58 is connected to the connection node between the first element 63 and the load 21 while the non-inversion input terminal of the operational amplifier 56 is connected to the connection node between the second element 64 and the third element 65. Based on the same concept as in the second embodiment, a condition for preventing occurrence of the lower limit clip in the operational amplifier 56 of the fourth embodiment shown in FIG. 10 is represented by the following Formula (9). If $V_{PSEUDO}$ is set to 0 in Formula (9), Formula (9) is the same as Formula (8).

$$R_1 \gtrsim \frac{(V_{OUT} + V_{PSEUDO}) \cdot R_2 + V_{PSEUDO} \cdot R_3}{(V_{OUT} - V_{PSEUDO}) \cdot R_3 - V_{PSEUDO} \cdot R_2} \cdot R_{HTR} \qquad (9)$$

In the fourth embodiment, as can be seen from Formula (9), the lower limit of the first electric resistance value $R_1$ is restricted. As described above, in order to improve the generation efficiency of the aerosol, the first electric resistance value $R_1$ is preferably minimized. Therefore, in the fourth embodiment, the first electric resistance value $R_1$ can be minimized by satisfying the following Formula (10).

$$R_3 > \frac{V_{OUT} + 2V_{PSEUDO}}{V_{OUT} - 2V_{PSEUDO}} \cdot R_2 \qquad (10)$$

Fifth Embodiment of Electric Circuit

Figure 11:
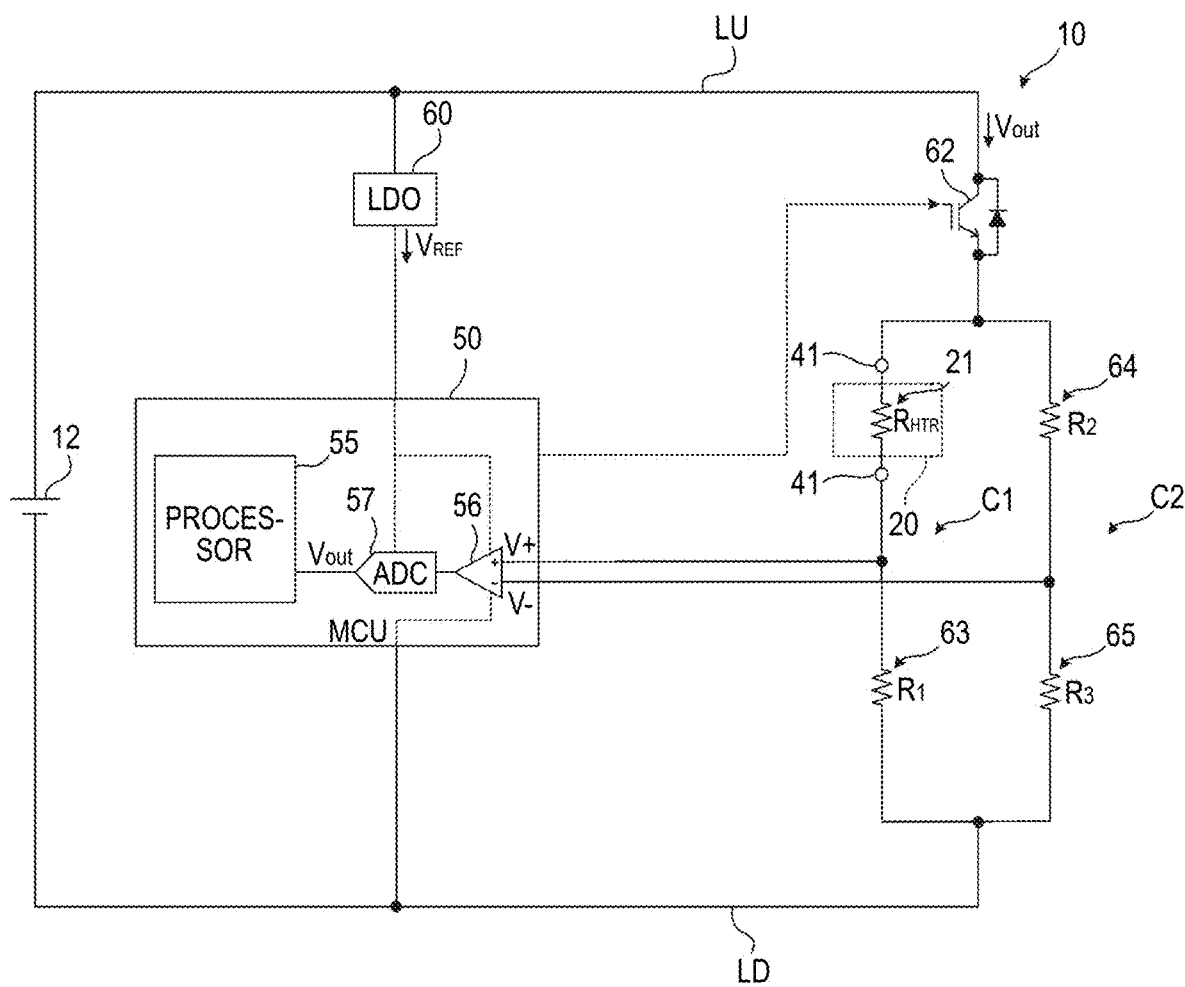
FIG. 11 is a schematic diagram showing a fifth embodiment of the circuit configuration of the power supply unit of the aerosol inhaler shown in FIG. 1.

FIG. 11 is a schematic diagram showing a fifth embodiment of the circuit configuration of the power supply unit of the aerosol inhaler shown in FIG. 1. The circuit shown in FIG. 11 is the same as the circuit configuration of FIG. 6 except that positions of the first element 63 and the load 21 in the first series circuit C1 are reversed. In the fifth embodiment shown in FIG. 11, in the first series circuit C1, the load 21 is connected to a high potential side of the first element 63. A condition for preventing occurrence of the lower limit clip in the operational amplifier 56 of the fifth embodiment is that $R_{HTR}$ and $R_1$ in Formula (5) are exchanged, so that the following Formula (11) is obtained.

$$R_1 \gtrsim \frac{R_3}{R_2} \cdot R_{HTR} \qquad (11)$$

In the fifth embodiment, as can be seen from Formula (11), the lower limit of the first electric resistance value $R_1$ is restricted. As described above, in order to improve the generation efficiency of the aerosol, the first electric resistance value $R_1$ is preferably minimized. Therefore, in the fifth embodiment, the first electric resistance value $R_1$ can be minimized by setting the second electric resistance value $R_2$ to be higher than the third electric resistance value $R_3$.

Sixth Embodiment of Electric Circuit

Figure 12:
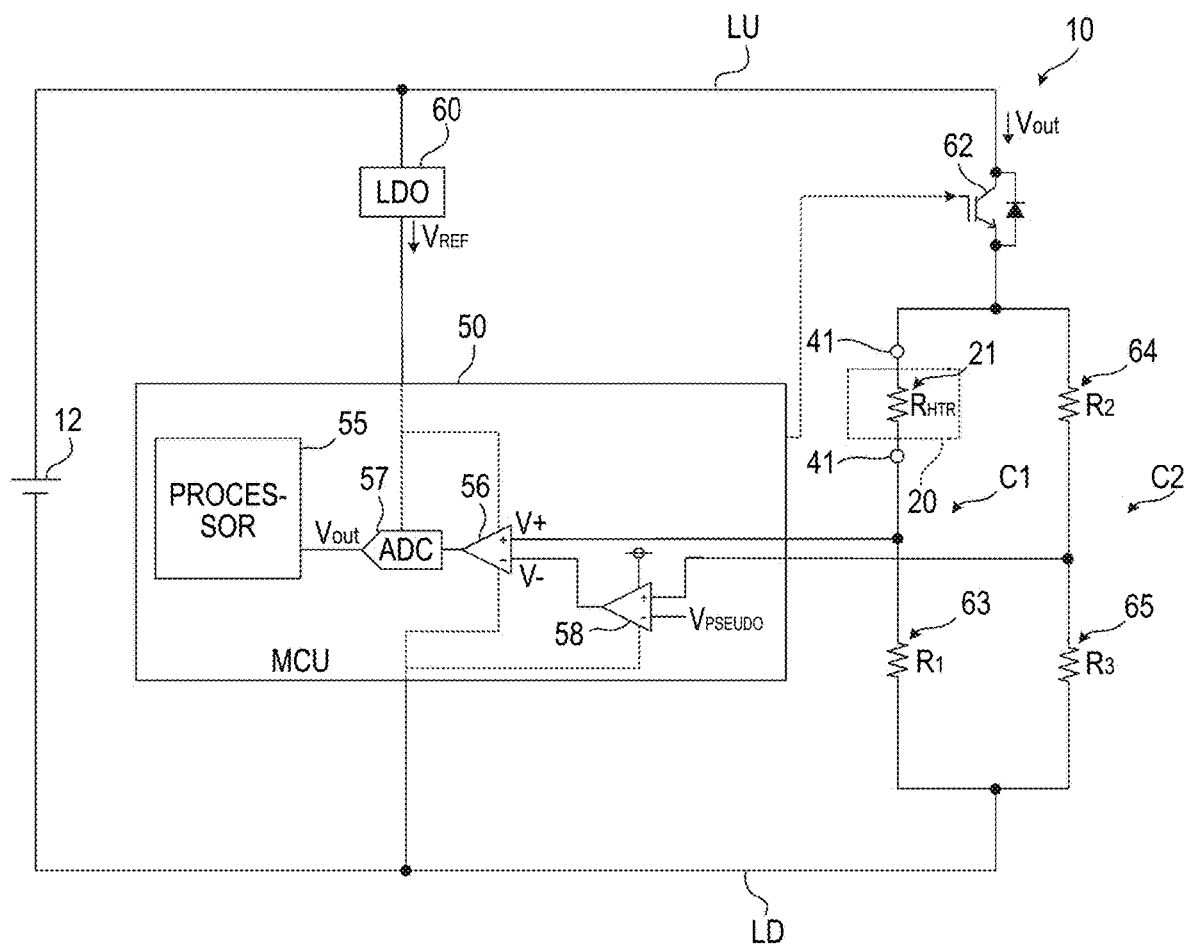
FIG. 12 is a schematic diagram showing a sixth embodiment of the circuit configuration of the power supply unit of the aerosol inhaler shown in FIG. 1.

FIG. 12 is a schematic diagram showing a sixth embodiment of the circuit configuration of the power supply unit of the aerosol inhaler shown in FIG. 1. The circuit shown in FIG. 12 is the same as the circuit configuration of FIG. 8 except that the positions of the first element 63 and the load 21 in the first series circuit C1 are reversed. In the sixth embodiment shown in FIG. 12, in the first series circuit C1, the load 21 is connected to the high potential side of the first element 63. A condition for preventing occurrence of the lower limit clip in the operational amplifier 56 of the sixth embodiment is that $R_{HTR}$ and $R_1$ in Formula (6) are exchanged, so that the following Formula (12) is obtained.

$$R_1 \gtrsim \frac{(V_{OUT} - V_{PSEUDO}) \cdot R_3 - V_{PSEUDO} \cdot R_2}{(V_{OUT} + V_{PSEUDO}) \cdot R_2 + V_{PSEUDO} \cdot R_3} \cdot R_{HTR} \quad (12)$$

In the sixth embodiment, as can be seen from Formula (12), the lower limit of the first electric resistance value $R_1$ is restricted. As described above, in order to improve the generation efficiency of the aerosol, the first electric resistance value $R_1$ is preferably minimized. Therefore, in the sixth embodiment, the first electric resistance value $R_1$ can be minimized by satisfying the following Formula (13).

$$R_3 < \frac{V_{OUT} + 2V_{PSEUDO}}{V_{OUT} - 2V_{PSEUDO}} \cdot R_2 \quad (13)$$

Seventh Embodiment of Electric Circuit

Figure 13:
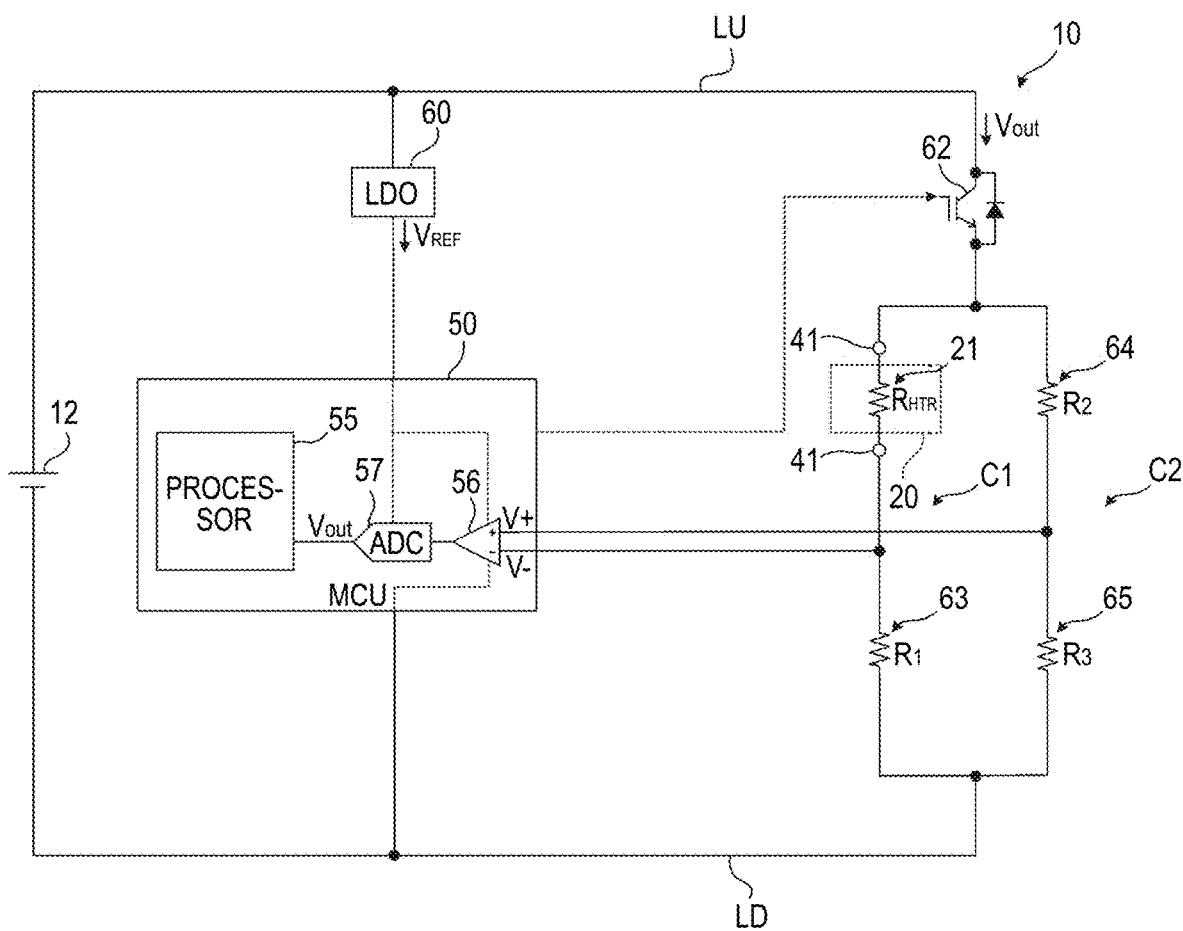
FIG. 13 is a schematic diagram showing a seventh embodiment of the circuit configuration of the power supply unit of the aerosol inhaler shown in FIG. 1.

FIG. 13 is a schematic diagram showing a seventh embodiment of the circuit configuration of the power supply unit of the aerosol inhaler shown in FIG. 1. The circuit shown in FIG. 13 is the same as the circuit configuration of FIG. 9 except that the positions of the first element 63 and the load 21 in the first series circuit C1 are reversed. In the seventh embodiment shown in FIG. 13, in the first series circuit C1, the load 21 is connected to the high potential side of the first element 63. A condition for preventing occurrence of the lower limit clip in the operational amplifier 56 of the seventh embodiment is that $R_{HTR}$ and $R_1$ in Formula (8) are exchanged, so that the following Formula (14) is obtained.

$$R_1 \lesssim \frac{R_3}{R_2} \cdot R_{HTR} \quad (14)$$

Eighth Embodiment of Electric Circuit

Figure 14:
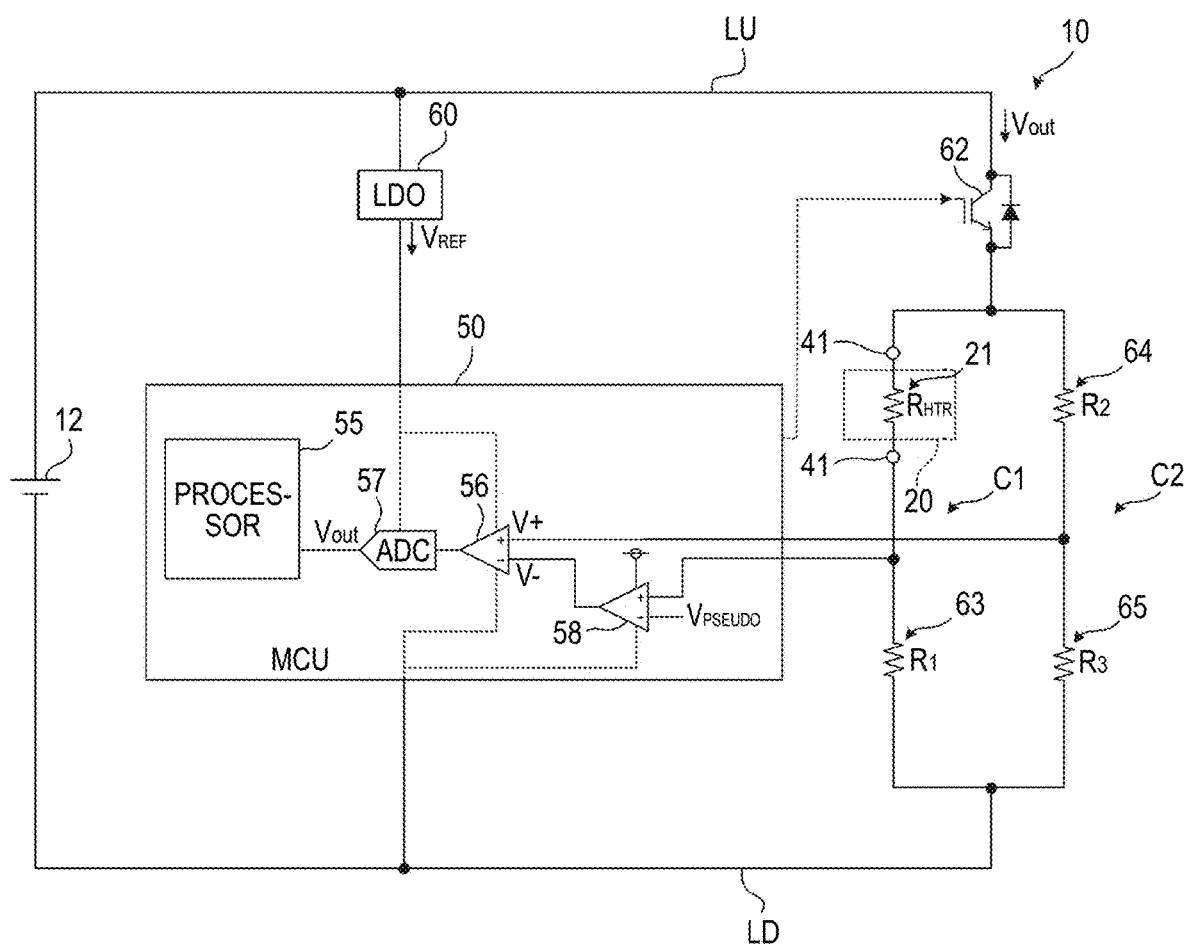
FIG. 14 is a schematic diagram showing an eighth embodiment of the circuit configuration of the power supply unit of the aerosol inhaler shown in FIG. 1.

FIG. 14 is a schematic diagram showing an eighth embodiment of the circuit configuration of the power supply unit of the aerosol inhaler shown in FIG. 1. The circuit shown in FIG. 14 is the same as the circuit configuration of FIG. 12 except that the non-inversion input terminal of the operational amplifier 58 is connected to the connection node between the first element 63 and the load 21 while the non-inversion input terminal of the operational amplifier 56 is connected to the connection node between the second element 64 and the third element 65. Based on the same concept as in the sixth embodiment, a condition for preventing occurrence of the lower limit clip in the operational amplifier 56 of the eighth embodiment shown in FIG. 14 is represented by the following Formula (15). If $V_{PSEUDO}$ is set to 0 in Formula (15), Formula (15) is the same as Formula (14).

$$R_1 \lesssim \frac{(V_{OUT} - V_{PSEUDO}) \cdot R_3 + V_{PSEUDO} \cdot R_2}{(V_{OUT} + V_{PSEUDO}) \cdot R_2 + V_{PSEUDO} \cdot R_3} \cdot R_{HTR} \quad (15)$$

FIG. 15 summarizes the respective configurations of the first to eighth embodiments and constraint conditions for preventing the occurrence of the lower limit clip. When the operational amplifier 56 used here is not an input-output rail-to-rail type operational amplifier, an inequality symbol with equality symbol of each constraint condition may be changed to an inequality symbol without equality symbol.

Effects of Embodiments

As described above, according to the power supply unit 10 including the electric circuits of the first to eighth embodiments, the first electric resistance value $R_1$ of the first element 63 is the lowest among the electric resistance values of the elements constituting the bridge circuit. Therefore, the power $P_{BRIDGE}$ consumed by the load 21 when power is supplied to the bridge circuit and the power $P_{BYPASS}$ consumed by the load 21 when power is supplied only to the load 21 as in the reference example can be close to each other. Therefore, even when power is supplied to the entire bridge circuit to measure the electric resistance value of the load 21, the aerosol generation efficiency of the load 21 can be sufficiently ensured. Moreover, according to the power supply unit 10, the switch 62 as in the reference example and control thereof are not necessary. Therefore, a manufacturing cost and power consumption can be reduced. Moreover, according to the power supply unit 10, since the electric resistance value of the entire bridge circuit can be reduced, it is possible to reduce the power consumption and the manufacturing cost.

As shown in FIG. 15, in the first embodiment, the second embodiment, the seventh embodiment, and the eighth embodiment, there is no restriction on the lower limit of the first electric resistance value $R_1$. Therefore, it is possible to easily improve the generation efficiency of the aerosol, and the present invention can thus be more preferably adopted.

Although the lower limit of the first electric resistance value $R_1$ is restricted in each of the third embodiment, the fourth embodiment, the fifth embodiment, and the sixth embodiment, there are methods for relaxing constraint conditions thereof. Therefore, the generation efficiency of the aerosol can be improved.

The first element 63 used here preferably has an electric resistance value equal to or higher than 10 mΩ and less than 0.5Ω, which is relatively easy to procure. As a result, the manufacturing cost can be reduced while the generation efficiency of the aerosol is improved.

The first element 63 used here also preferably has an electric resistance value equal to or higher than 1 mΩ and less than 10 mΩ. As a result, the manufacturing cost can be reduced while the generation efficiency of the aerosol is further improved.

The first element 63 used here also preferably has an electric resistance value equal to or higher than 0.1 mΩ and less than 1 mΩ. As a result, since the electric resistance value of the first element can be minimized, the generation efficiency of the aerosol can be maximized.

First Modification of Electric Circuit

Figure 16:
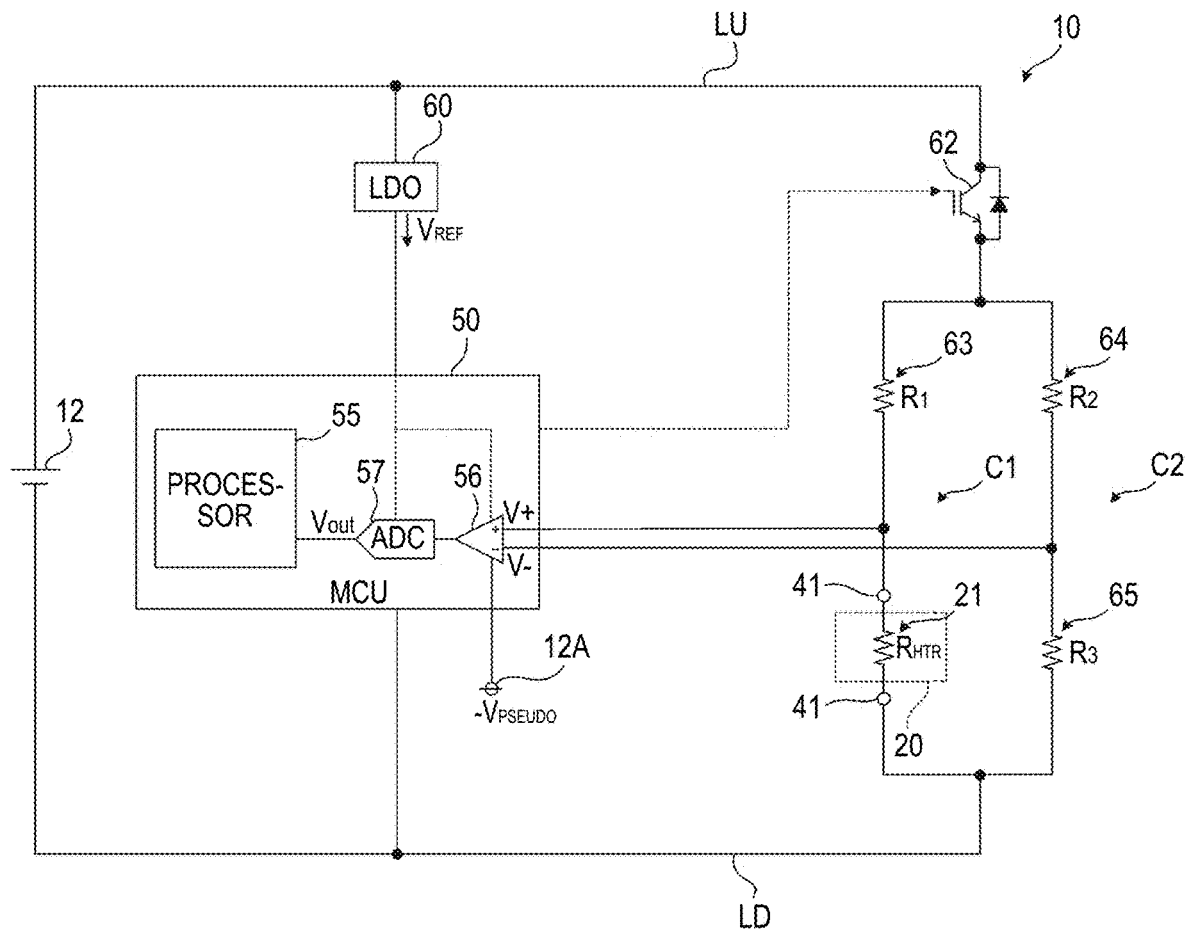
FIG. 16 is a schematic diagram showing a first modification of the circuit shown in FIG. 6.

FIG. 16 is a schematic diagram showing a first modification of the electric circuit shown in FIG. 6. The circuit shown in FIG. 16 has the same configuration as that of FIG. 6 except that the negative power supply terminal of the operational amplifier 56 is connected to a power supply 12A that supplies a negative default potential $V_{PSEUDO}$. The negative default potential $V_{PSEUDO}$ is generated, for example, from the reference voltage $V_{REF}$.

As compared with the first embodiment shown in FIG. 6, the potential of the negative power supply terminal of the operational amplifier 56 is negative in the circuit shown in FIG. 16, so that it is possible to prevent the occurrence of the lower limit clip even when the potential of the connection node between the first element 63 and the load 21 is lower than the potential of the connection node between the second element 64 and the third element 65. Therefore, it is possible to detect the temperature of the load 21 with high accuracy.

In order to prevent occurrence of the lower limit clip in the operational amplifier 56 of the circuit shown in FIG. 16, it is necessary to satisfy a conditional expression of $(V_+ - V_-) \geq (-V_{PSEUDO})$. This conditional expression is the same as a conditional expression of $[V_+ - (V_- - V_{PSEUDO}) \geq 0]$ in Formula (6). Therefore, the electric resistance values of the elements of the bridge circuit in the circuit shown in FIG. 16 preferably satisfy the same conditions as those of the circuit of the second embodiment. Similarly, a configuration in which the potential of the negative power supply terminal of the operational amplifier 56 is changed to $-V_{PSEUDO}$ instead of the operational amplifier 58 can be applied to each of the fourth embodiment, the sixth embodiment, and the eighth embodiment.

Second Modification of Electric Circuit

Figure 17:
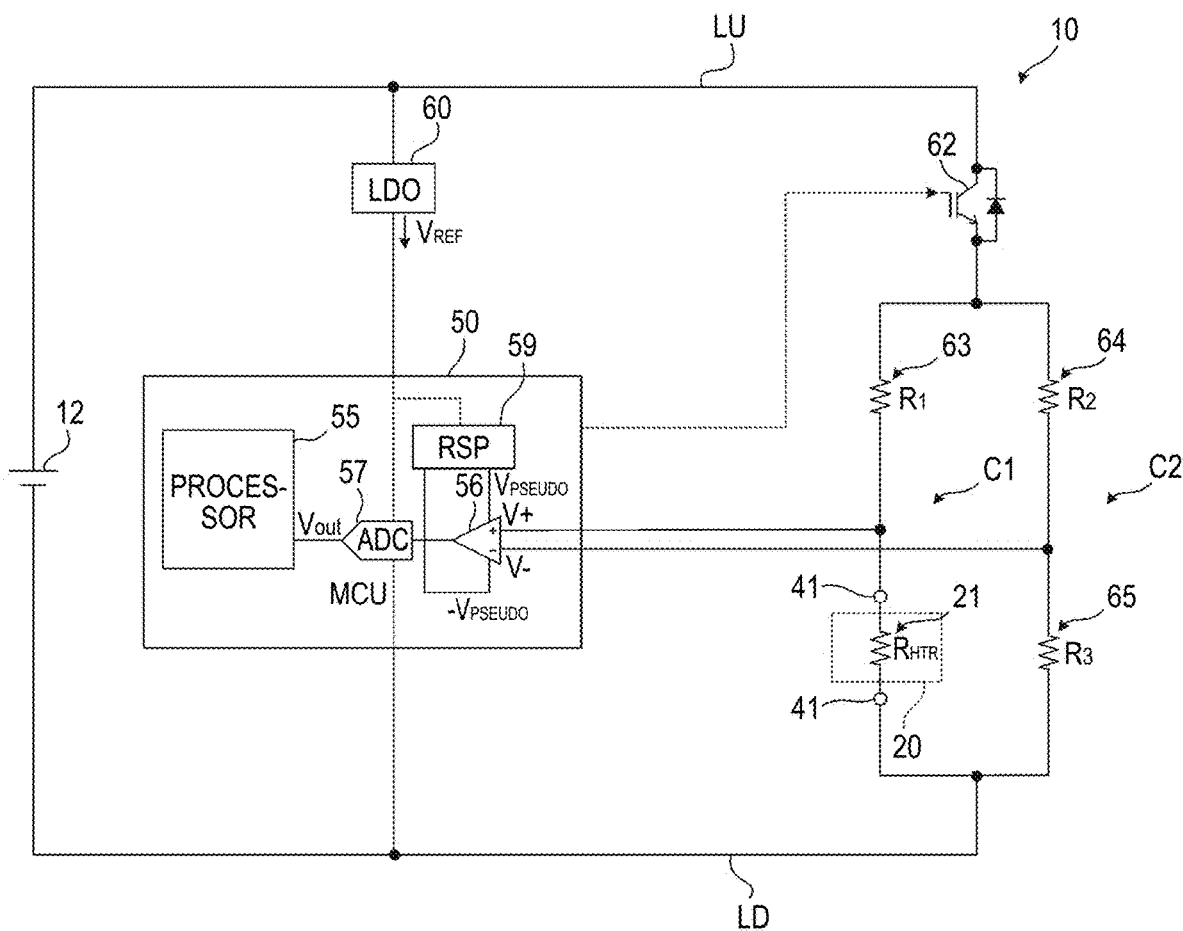
FIG. 17 is a schematic diagram showing a second modification of the circuit shown in FIG. 6.

FIG. 17 is a schematic diagram showing a second modification of the electric circuit shown in FIG. 6. The circuit shown in FIG. 17 has the same configuration as FIG. 6 except that a rail splitter 59 is added and a voltage is supplied from the rail splitter 59 to the two power supply terminals of the operational amplifier 56.

The rail splitter 59 generates, from the reference voltage $V_{REF}$, a voltage of $V_{REF}/2$ which serves as $V_{PSEUDO}$ and a voltage of $(-V_{REF}/2)$ which serves as $(-V_{PSEUDO})$. The voltage $V_{PSEUDO}$ generated by the rail splitter 59 is supplied to the positive power supply terminal of the operational amplifier 56, and the voltage $(-V_{PSEUDO})$ generated by the rail splitter 59 is supplied to the negative power supply terminal of the operational amplifier 56.

In order to prevent occurrence of the lower limit clip in the operational amplifier 56 of the circuit shown in FIG. 17, it is necessary to satisfy the conditional expression of $(V_+ - V_-) \geq (-V_{PSEUDO})$. This conditional expression is the same as the conditional expression of $[V+ - (V_- - V_{PSEUDO}) \geq 0]$ in Formula (6). Therefore, the electric resistance values of the elements of the bridge circuit in the circuit shown in FIG. 17 preferably satisfy the same conditions as those of the circuit of the second embodiment. Similarly, a configuration in which the rail splitter 59 is added instead of the operational amplifier 58 can be applied to each of the fourth embodiment, the sixth embodiment, and the eighth embodiment.

Although the first cartridge 20 including the load 21 is detachably attached to the power supply unit 10 in the above-described embodiments, the first cartridge 20 including the load 21 may also be integrated with the power supply unit 10.

At least the following matters are described in the present specification. Although corresponding constituent elements or the like in the above embodiments are shown in parentheses, the present invention is not limited thereto.

(1)

A power supply unit (power supply unit 10) for an aerosol inhaler (aerosol inhaler 1). The aerosol inhaler includes a power supply (power supply 12) configured to discharge electricity to a load (load 21) that is configured to heat an aerosol generation source and has a correlation between temperature and electric resistance values. The power supply unit for the aerosol inhaler includes:

a first element (first element 63) connected in series to the load and having a first electric resistance value (first electric resistance value $R_1$);

a second series circuit (second series circuit C2) that includes a second element (second element 64) having a second electric resistance value (second electric resistance value $R_2$) and a third element (third element 65) connected in series to the second element and having a third electric resistance value (third electric resistance value $R_3$), the second series circuit being connected in parallel with a first series circuit (first series circuit C1) including the load and the first element; and an operational amplifier (operational amplifier 56) connected to the first series circuit and the second series circuit.

The first electric resistance value is less than an electric resistance value of the load.

According to (1), power consumed by the load when power is supplied to the first series circuit and the second series circuit, and power consumed by the load when power is supplied only to the load can be close to each other. Therefore, even when power is supplied to the first series circuit and the second series circuit to measure the electric resistance value of the load, aerosol generation efficiency of the load can be sufficiently ensured.

(2)

The power supply unit for the aerosol inhaler according to (1), in which the first element has a lowest electric resistance value among the load, the first element, the second element, and the third element.

According to (2), the combined resistance value of the first series circuit including the load, for which a load having a low electric resistance value is likely to be used, and the first element can be smaller than a combined resistance value of the second series circuit so as to generate a sufficient amount of aerosol. Therefore, even when power is supplied to the first series circuit and the second series circuit to measure the electric resistance value of the load, a large amount of power can be supplied to the load, and thus the generation efficiency of the aerosol can be improved.

(3)

The power supply unit for the aerosol inhaler according to (1), in which a combined resistance value of the second electric resistance value and the third electric resistance value is larger than a combined resistance value of the electric resistance value of the load and the first electric resistance value.

According to (3), even when power is supplied to the first series circuit and the second series circuit to measure the electric resistance value of the load, the power is preferentially supplied to the first series circuit. As a result, a large amount of power can be supplied to the load, and thus the generation efficiency of the aerosol can be improved.

(4)

The power supply unit for the aerosol inhaler according to (1), in which the first electric resistance value is equal to or larger than 10 mΩ and less than 0.5Ω.

According to (4), an element used as the first element can have an electric resistance value smaller than that of a mainly used load whose electric resistance value is about 0.8 to 1.5Ω and be relatively easy to procure. Therefore, the generation efficiency of the aerosol can be improved at a low cost.

(5)

The power supply unit for the aerosol inhaler according to (1), in which the first electric resistance value is equal to or larger than 1 mΩ and less than 10 mΩ.

According to (5), the element used as the first element can have an electric resistance value smaller than that of the mainly used load whose electric resistance value is about 0.8 to 1.5Ω and be relatively easy to procure. Therefore, the generation efficiency of the aerosol can be improved at a low cost.

(6)

The power supply unit for the aerosol inhaler according to (1), in which the first electric resistance value is equal to or larger than 0.1 mΩ and less than 1 mΩ.

According to (6), since the electric resistance value of the first element can be minimized, the generation efficiency of the aerosol can be maximized.

(7)

The power supply unit for the aerosol inhaler according to (1), in which a non-inversion input terminal of the operational amplifier is connected to the first series circuit, an inversion input terminal of the operational amplifier is connected to the second series circuit, and the first element is connected to a high potential side of the load.

According to (7), no constraint condition (lower limit) is added to the first electric resistance value for preventing a differential input of the operational amplifier from being clipped to a negative power supply potential. Therefore, the first electric resistance value is easily reduced, and the generation efficiency of the aerosol can be easily improved.

(8)

The power supply unit for the aerosol inhaler according to (7), in which the first electric resistance value is equal to or less than a value determined based on the second electric resistance value, the third electric resistance value, and the electric resistance value of the load.

According to (8), the differential input of the operational amplifier can be easily prevented from being clipped to the negative power supply potential. Therefore, improvement of the generation efficiency of the aerosol and accurate measurement of the electric resistance value of the load can both be achieved.

(9)

The power supply unit for the aerosol inhaler according to (7) or (8), in which when the first electric resistance value is represented by $R_1$, the second electric resistance value is represented by $R_2$, the third electric resistance value is represented by $R_3$, and the electric resistance value of the load is represented by $R_{HTR}$, $$R_1 \leq \frac{R_2}{R_3} \cdot R_{HTR} \quad (I)$$

the formula (I) is satisfied.

According to (9), the differential input of the operational amplifier can be easily prevented from being clipped to the negative power supply potential. Therefore, the improvement of the generation efficiency of the aerosol and the accurate measurement of the electric resistance value of the load can both be achieved.

(10)

The power supply unit for the aerosol inhaler according to (7), in which a negative default potential ($V_{PSEUDO}$) is input to a negative power supply terminal of the operational amplifier, or a circuit (operational amplifier 58) configured to subtract the default potential from a potential of a node which is electrically connected to the inversion input terminal of the operational amplifier in the second series circuit is provided, and the first electric resistance value is equal to or less than a value determined based on a voltage applied to the first series circuit and the second series circuit, the default potential, the second electric resistance value, the third electric resistance value, and the electric resistance value of the load.

According to (10), the differential input of the operational amplifier can be more easily prevented, by the default potential, from being clipped to the negative power supply potential. Therefore, the improvement of the generation efficiency of the aerosol and more accurate measurement of the electric resistance value of the load can both be achieved.

(11)

The power supply unit for the aerosol inhaler according to (7), in which a negative default potential ($V_{PSEUDO}$) is input to a negative power supply terminal of the operational amplifier, or a circuit (operational amplifier 58) configured to subtract the default potential from a potential of a node which is electrically connected to the inversion input terminal of the operational amplifier in the second series circuit is provided, and when the first electric resistance value is represented by $R_1$, the second electric resistance value is represented by $R_2$, the third electric resistance value is represented by $R_3$, the electric resistance value of the load is represented by $R_{HTR}$, the voltage is represented by $V_{OUT}$, and the default potential is represented by $V_{PSEUDO}$, $$R_1 \leqq \frac{(V_{OUT} + V_{PSEUDO}) \cdot R_2 + V_{PSEUDO} \cdot R_3}{(V_{OUT} - V_{PSEUDO}) \cdot R_3 - V_{PSEUDO} \cdot R_2} \cdot R_{HTR} \tag{II}$$

the formula (II) is satisfied.

According to (11), the differential input of the operational amplifier can be more easily prevented, by the default potential, from being clipped to the negative power supply potential. Therefore, the improvement of the generation efficiency of the aerosol and more accurate measurement of the electric resistance value of the load can both be achieved.

(12)

The power supply unit for the aerosol inhaler according to (1), in which a non-inversion input terminal of the operational amplifier is connected to the second series circuit, an inversion input terminal of the operational amplifier is connected to the first series circuit, and the first element is connected to a low potential side of the load.

According to (12), no constraint condition (lower limit) is added to the first electric resistance value for preventing the differential input of the operational amplifier from being clipped to the negative power supply potential. Therefore, the first electric resistance value can be easily reduced, and the generation efficiency of the aerosol can be easily improved.

(13)

The power supply unit for the aerosol inhaler according to (12), in which the first electric resistance value is equal to or less than a value determined based on the second electric resistance value, the third electric resistance value, and the electric resistance value of the load.

According to (13), the differential input of the operational amplifier can be easily prevented from being clipped to the negative power supply potential. Therefore, the improvement of the generation efficiency of the aerosol and the accurate measurement of the electric resistance value of the load can both be achieved.

(14)

The power supply unit for the aerosol inhaler according to (12) or (13), in which when the first electric resistance value is represented by $R_1$, the second electric resistance value is represented by $R_2$, the third electric resistance value is represented by $R_3$, and the electric resistance value of the load is represented by $R_{HTR}$, $$R_1 \leqq \frac{R_3}{R_2} \cdot R_{HTR} \quad (III)$$

the formula (III) is satisfied.

According to (14), the differential input of the operational amplifier can be easily prevented from being clipped to the negative power supply potential. Therefore, the improvement of the generation efficiency of the aerosol and the accurate measurement of the electric resistance value of the load can both be achieved.

(15)

The power supply unit for the aerosol inhaler according to (12), in which a negative default potential ($V_{PSEUDO}$) is input to a negative power supply terminal of the operational amplifier, or a circuit (operational amplifier 58) configured to subtract the default potential from a potential of a node which is electrically connected to the inversion input terminal of the operational amplifier in the first series circuit is provided, and the first electric resistance value is equal to or less than a value determined based on a voltage applied to the first series circuit and the second series circuit, the default potential, the second electric resistance value, the third electric resistance value, and the electric resistance value of the load.

According to (15), the differential input of the operational amplifier can be more easily prevented, by the default potential, from being clipped to the negative power supply potential. Therefore, the improvement of the generation efficiency of the aerosol and more accurate measurement of the electric resistance value of the load can both be achieved.

(16)

The power supply unit for the aerosol inhaler according to (12), in which a negative default potential ($V_{PSEUDO}$) is input to a negative power supply terminal of the operational amplifier, or a circuit (operational amplifier 58) configured to subtract the default potential from a potential of a node which is electrically connected to the inversion input terminal of the operational amplifier in the first series circuit is provided, and when the first electric resistance value is represented by $R_1$, the second electric resistance value is represented by $R_2$, the third electric resistance value is represented by $R_3$, the electric resistance value of the load is represented by $R_{HTR}$, the voltage is represented by $V_{OUT}$, and the default potential is represented by $V_{PSEUDO}$, $$R_1 \leqq \frac{(V_{OUT} - V_{PSEUDO}) \cdot R_3 + V_{PSEUDO} \cdot R_2}{(V_{OUT} + V_{PSEUDO}) \cdot R_2 + V_{PSEUDO} \cdot R_3} \cdot R_{HTR} \quad (IV)$$

the formula (IV) is satisfied.

According to (16), the differential input of the operational amplifier can be more easily prevented, by the default potential, from being clipped to the negative power supply potential. Therefore, the improvement of the generation efficiency of the aerosol and more accurate measurement of the electric resistance value of the load can both be achieved.

(17)

The power supply unit for the aerosol inhaler according to (1), in which a non-inversion input terminal of the operational amplifier is connected to the second series circuit, an inversion input terminal of the operational amplifier is connected to the first series circuit, the first element is connected to a high potential side of the load, and when the first electric resistance value is represented by $R_1$, the second electric resistance value is represented by $R_2$, the third electric resistance value is represented by $R_3$, and the electric resistance value of the load is represented by $R_{HTR}$, $$R_1 \geqq \frac{R_2}{R_3} \cdot R_{HTR} \quad (V)$$

the formula (V) is satisfied.

According to (17), the differential input of the operational amplifier can be prevented from being clipped to the negative power supply potential. Therefore, the improvement of the generation efficiency of the aerosol and the accurate measurement of the electric resistance value of the load can both be achieved.

(18)

The power supply unit for the aerosol inhaler according to (17), in which a relationship of $R_3 > R_2$ is satisfied.

According to (18), a constraint condition of the first electric resistance value for preventing the differential input of the operational amplifier from being clipped to the negative power supply potential can be relaxed. Therefore, the first electric resistance value is easily reduced, and the generation efficiency of the aerosol can be easily improved.

(19)

The power supply unit for the aerosol inhaler according to (1), in which a non-inversion input terminal of the operational amplifier is connected to the second series circuit, an inversion input terminal of the operational amplifier is connected to the first series circuit, the first element is connected to a high potential side of the load, a negative default potential ($V_{PSEUDO}$) is input to a negative power supply terminal of the operational amplifier, or a circuit (operational amplifier 58) configured to subtract the default potential from a potential of a node which is electrically connected to the inversion input terminal of the operational amplifier in the first series circuit is provided, and when the first electric resistance value is represented by $R_1$, the second electric resistance value is represented by $R_2$, the third electric resistance value is represented by $R_3$, the electric resistance value of the load is represented by $R_{HTR}$, a voltage applied to the first series circuit and the second series circuit is represented by $V_{OUT}$, and the default potential is represented by $V_{PSEUDO}$, $$R_1 \geq \frac{(V_{OUT} + V_{PSEUDO}) \cdot R_2 + V_{PSEDUDO} \cdot R_3}{(V_{OUT} - V_{PSEUDO}) \cdot R_3 - V_{PSEDUDO} \cdot R_2} \cdot R_{HTR} \quad \text{(VI)}$$

the formula (VI) is satisfied.

According to (19), the differential input of the operational amplifier can be further prevented, by the default potential, from being clipped to the negative power supply potential. Therefore, the improvement of the generation efficiency of the aerosol and more accurate measurement of the electric resistance value of the load can both be achieved.

(20)

The power supply unit for the aerosol inhaler according to (19), in which $$R_3 > \frac{V_{OUT} + 2V_{PSEUDO}}{V_{OUT} - 2V_{PSEUDO}} \cdot R_2 \quad \text{(VII)}$$

the formula (VII) is satisfied.

According to (20), the constraint condition of the first electric resistance value for further preventing the differential input of the operational amplifier by the default potential from being clipped to the negative power supply potential can be relaxed. Therefore, the first electric resistance value is easily reduced, and the generation efficiency of the aerosol can be easily improved.

(21)

The power supply unit for the aerosol inhaler according to (1), in which a non-inversion input terminal of the operational amplifier is connected to the first series circuit, an inversion input terminal of the operational amplifier is connected to the second series circuit, the first element is connected to a low potential side of the load, and when the first electric resistance value is represented by $R_1$, the second electric resistance value is represented by $R_2$, the third electric resistance value is represented by $R_3$, and the electric resistance value of the load is represented by $R_{HTR}$, $$R_1 \geq \frac{R_3}{R_2} \cdot R_{HTR} \quad \text{(VIII)}$$

the formula (VIII) is satisfied.

According to (21), the differential input of the operational amplifier can be prevented from being clipped to the negative power supply potential. Therefore, the improvement of the generation efficiency of the aerosol and the accurate measurement of the electric resistance value of the load can both be achieved.

(22)

The power supply unit for the aerosol inhaler according to (21), in which a relationship of $R_2 > R_3$ is satisfied.

According to (22), the constraint condition of the first electric resistance value for preventing the differential input of the operational amplifier from being clipped to the negative power supply potential can be relaxed. Therefore, the first electric resistance value is easily reduced, and the generation efficiency of the aerosol can be easily improved.

(23)

The power supply unit for the aerosol inhaler according to (1), in which a non-inversion input terminal of the operational amplifier is connected to the first series circuit, an inversion input terminal of the operational amplifier is connected to the second series circuit, the first element is connected to a low potential side of the load, a negative default potential ($V_{PSEUDO}$) is input to a negative power supply terminal of the operational amplifier, or a circuit (operational amplifier) configured to subtract the default potential from a potential of a node which is electrically connected to the inversion input terminal of the operational amplifier in the second series circuit is provided, and when the first electric resistance value is represented by $R_1$, the second electric resistance value is represented by $R_2$, the third electric resistance value is represented by $R_3$, the electric resistance value of the load is represented by $R_{HTR}$, a voltage applied to the first series circuit and the second series circuit is represented by $V_{OUT}$, and the default potential is represented by $V_{PSEUDO}$, $$R_1 \geq \frac{(V_{OUT} - V_{PSEUDO}) \cdot R_3 - V_{PSEDUDO} \cdot R_2}{(V_{OUT} + V_{PSEUDO}) \cdot R_2 + V_{PSEDUDO} \cdot R_3} \cdot R_{HTR} \quad \text{(IX)}$$

the formula (IX) is satisfied.

According to (23), the differential input of the operational amplifier can be prevented from being clipped to the negative power supply potential. Therefore, the improvement of the generation efficiency of the aerosol and the accurate measurement of the electric resistance value of the load can both be achieved.

(24)

The power supply unit for the aerosol inhaler according to (23), in which $$R_3 < \frac{V_{OUT} + 2V_{PSEUDO}}{V_{OUT} - 2V_{PSEUDO}} \cdot R_2 \quad \text{(X)}$$

the formula (X) is satisfied.

According to (24), the constraint condition of the first electric resistance value for preventing the differential input of the operational amplifier from being clipped to the negative power supply potential can be relaxed. Therefore, the first electric resistance value is easily reduced, and the generation efficiency of the aerosol can be easily improved.

(25)

The power supply unit for the aerosol inhaler according to (1), further includes a control device (MCU 50) configured to supply power to the first series circuit and the second series circuit such that the load generates aerosol from the aerosol generation source based on an aerosol generation request.

According to (25), even when power is supplied to the first series circuit and the second series circuit, sufficient power can be supplied to the load. Therefore, even when there is no addition of a circuit for supplying power only to the load, sufficient aerosol generation efficiency can be achieved.

(26)

The power supply unit for the aerosol inhaler according to (25), in which the control device is configured to acquire a temperature of the load based on an output of the operational amplifier while supplying the power to the first series circuit and the second series circuit such that the load generates the aerosol from the aerosol generation source.

According to (26), since the temperature of the load can be acquired during generation of the aerosol, accuracy of control of the load using the temperature of the load and speed of such control can be improved.

The invention claimed is:

1. A power supply unit for an aerosol inhaler, the aerosol inhaler including a power supply configured to discharge electricity to a load that is configured to heat an aerosol generation source and has a correlation between temperature and electric resistance values, the power supply unit for the aerosol inhaler comprising:
   a first element connected in series to the load and having a first electric resistance value;
   a second series circuit that includes a second element having a second electric resistance value and a third element connected in series to the second element and having a third electric resistance value; and
   an operational amplifier, wherein
   the second series circuit is connected in parallel with a first series circuit including the load and the first element,
   the operational amplifier is connected to the first series circuit and the second series circuit,
   a temperature of the load is detected based on an output signal of the operational amplifier,
   the first electric resistance value is less than an electric resistance value of the load,
   the first series circuit is connected to one of a non-inversion input terminal and an inversion input terminal of the operational amplifier, in between the first element and the load, and
   the second series circuit is connected to the other of the non-inversion input terminal and the inversion input terminal of the operational amplifier, in between the second element and the third element.

2. The power supply unit for the aerosol inhaler according to claim 1, wherein
   the first element has a lowest electric resistance value among the load, the first element, the second element, and the third element.

3. The power supply unit for the aerosol inhaler according to claim 1, wherein
   a combined resistance value of the second electric resistance value and the third electric resistance value is larger than a combined resistance value of the electric resistance value of the load and the first electric resistance value.

4. The power supply unit for the aerosol inhaler according to claim 1, wherein
   the first electric resistance value is equal to or larger than 10 mΩ and less than 0.5Ω.

5. The power supply unit for the aerosol inhaler according to claim 1, wherein
   the first electric resistance value is equal to or larger than 1 mΩ and less than 10 mΩ.

6. The power supply unit for the aerosol inhaler according to claim 1, wherein
   the first electric resistance value is equal to or larger than 0.1 mΩ and less than 1 mΩ.

7. The power supply unit for the aerosol inhaler according to claim 1, wherein
   a connection node between the load and the first element is connected to one of the non-inversion input terminal and the inversion input terminal of the operational amplifier in the first series circuit, and a connection node between the second element and the third element is connected to the other of the non-inversion input terminal and the inversion input terminal of the operational amplifier in the second series circuit.

8. The power supply unit for the aerosol inhaler according to claim 7, wherein
   the non-inversion input terminal of the operational amplifier is connected to the connection node of the first series circuit,
   the inversion input terminal of the operational amplifier is connected to the connection node of the second series circuit, and
   the first element is connected to a high potential side of the load.

9. The power supply unit for the aerosol inhaler according to claim 8, wherein
   the first electric resistance value is equal to or less than a value determined based on the second electric resistance value, the third electric resistance value, and the electric resistance value of the load.

10. The power supply unit for the aerosol inhaler according to claim 8, wherein
    when the first electric resistance value is represented by $R_1$, the second electric resistance value is represented by $R_2$, the third electric resistance value is represented by $R_3$, and the electric resistance value of the load is represented by $R_{HTR}$, $$R_1 \leq \frac{R_2}{R_3} \cdot R_{HTR} \quad (\mathrm{I})$$

the formula (I) is satisfied.

11. The power supply unit for the aerosol inhaler according to claim 8, wherein
    a negative default potential is input to a negative power supply terminal of the operational amplifier, or a circuit configured to subtract the default potential from a potential of the connection node which is electrically connected to the inversion input terminal of the operational amplifier in the second series circuit is provided, and
    the first electric resistance value is equal to or less than a value determined based on a voltage applied to the first series circuit and the second series circuit, the default potential, the second electric resistance value, the third electric resistance value, and the electric resistance value of the load.

12. The power supply unit for the aerosol inhaler according to claim 8, wherein
    a negative default potential is input to a negative power supply terminal of the operational amplifier, or a circuit configured to subtract the default potential from a potential of the connection node which is electrically connected to the inversion input terminal of the operational amplifier in the second series circuit is provided, and when the first electric resistance value is represented by $R_1$, the second electric resistance value is represented by $R_2$, the third electric resistance value is represented by $R_3$, the electric resistance value of the load is represented by $R_{HTR}$, the voltage applied to the first series circuit and the second series circuit is represented by $V_{OUT}$, and the default potential is represented by $V_{PSEUDO}$, $$R_1 \leq \frac{(V_{OUT} + V_{PSEUDO}) \cdot R_2 + V_{PSEDUDO} \cdot R_3}{(V_{OUT} - V_{PSEUDO}) \cdot R_3 - V_{PSEDUDO} \cdot R_2} \cdot R_{HTR} \quad (II)$$

the formula (II) is satisfied.

13. The power supply unit for the aerosol inhaler according to claim 7, wherein
the non-inversion input terminal of the operational amplifier is connected to the connection node of the second series circuit,
the inversion input terminal of the operational amplifier is connected to the connection node of the first series circuit, and
the first element is connected to a low potential side of the load.

14. The power supply unit for the aerosol inhaler according to claim 13, wherein
the first electric resistance value is equal to or less than a value determined based on the second electric resistance value, the third electric resistance value, and the electric resistance value of the load.

15. The power supply unit for the aerosol inhaler according to claim 13, wherein
when the first electric resistance value is represented by $R_1$, the second electric resistance value is represented by $R_2$, the third electric resistance value is represented by $R_3$, and the electric resistance value of the load is represented by $R_{HTR}$, $$R_1 \leq \frac{R_3}{R_2} \cdot R_{HTR} \quad (III)$$

the formula (III) is satisfied.

16. The power supply unit for the aerosol inhaler according to claim 13, wherein
a negative default potential is input to a negative power supply terminal of the operational amplifier, or a circuit configured to subtract the default potential from a potential of the connection node which is electrically connected to the inversion input terminal of the operational amplifier in the first series circuit is provided, and
the first electric resistance value is equal to or less than a value determined based on a voltage applied to the first series circuit and the second series circuit, the default potential, the second electric resistance value, the third electric resistance value, and the electric resistance value of the load.

17. The power supply unit for the aerosol inhaler according to claim 13, wherein
a negative default potential is input to a negative power supply terminal of the operational amplifier, or a circuit configured to subtract the default potential from a potential of the connection node which is electrically connected to the inversion input terminal of the operational amplifier in the first series circuit is provided, and when the first electric resistance value is represented by $R_1$, the second electric resistance value is represented by $R_2$, the third electric resistance value is represented by $R_3$, the electric resistance value of the load is represented by $R_{HTR}$, the voltage applied to the first series circuit and the second series circuit is represented by $V_{OUT}$, and the default potential is represented by $V_{PSEUDO}$, $$R_1 \leq \frac{(V_{OUT} - V_{PSEUDO}) \cdot R_3 + V_{PSEUDO} \cdot R_2}{(V_{OUT} + V_{PSEUDO}) \cdot R_2 + V_{PSEDUDO} \cdot R_3} \cdot R_{HTR} \quad (IV)$$

the formula (IV) is satisfied.

18. The power supply unit for the aerosol inhaler according to claim 7, wherein
the non-inversion input terminal of the operational amplifier is connected to the connection node of the second series circuit,
the inversion input terminal of the operational amplifier is connected to the connection node of the first series circuit,
the first element is connected to a high potential side of the load, and
when the first electric resistance value is represented by $R_1$, the second electric resistance value is represented by $R_2$, the third electric resistance value is represented by $R_3$, and the electric resistance value of the load is represented by $R_{HTR}$, $$R_1 \geq \frac{R_2}{R_3} \cdot R_{HTR} \quad (V)$$

the formula (V) is satisfied.

19. The power supply unit for the aerosol inhaler according to claim 18, wherein
a relationship of $R_3 > R_2$ is satisfied.

20. The power supply unit for the aerosol inhaler according to claim 7, wherein
the non-inversion input terminal of the operational amplifier is connected to the connection node of the second series circuit,
the inversion input terminal of the operational amplifier is connected to the connection node of the first series circuit,
the first element is connected to a high potential side of the load,
a negative default potential is input to a negative power supply terminal of the operational amplifier, or a circuit configured to subtract the default potential from a potential of the connection node which is electrically connected to the inversion input terminal of the operational amplifier in the first series circuit is provided, and
when the first electric resistance value is represented by $R_1$, the second electric resistance value is represented by $R_2$, the third electric resistance value is represented by $R_3$, the electric resistance value of the load is represented by $R_{HTR}$, a voltage applied to the first series circuit and the second series circuit is represented by $V_{OUT}$, and the default potential is represented by $V_{PSEUDO}$, $$R_1 \geq \frac{(V_{OUT} + V_{PSEUDO}) \cdot R_2 + V_{PSEDUDO} \cdot R_3}{(V_{OUT} - V_{PSEUDO}) \cdot R_3 - V_{PSEDUDO} \cdot R_2} \cdot R_{HTR} \quad \text{(VI)}$$

the formula (VI) is satisfied.

21. The power supply unit for the aerosol inhaler according to claim 20, wherein $$R_3 > \frac{V_{OUT} + 2V_{PSEUDO}}{V_{OUT} - 2V_{PSEUDO}} \cdot R_2 \quad \text{(VII)}$$

the formula (VII) is satisfied.

22. The power supply unit for the aerosol inhaler according to claim 7, wherein
the non-inversion input terminal of the operational amplifier is connected to the connection node of the first series circuit,
the inversion input terminal of the operational amplifier is connected to the connection node of the second series circuit,
the first element is connected to a low potential side of the load, and
when the first electric resistance value is represented by $R_1$, the second electric resistance value is represented by $R_2$, the third electric resistance value is represented by $R_3$, and the electric resistance value of the load is represented by $R_{HTR}$, $$R_1 \geq \frac{R_3}{R_2} \cdot R_{HTR} \quad \text{(VIII)}$$

the formula (VIII) is satisfied.

23. The power supply unit for the aerosol inhaler according to claim 22, wherein
a relationship of $R_2 > R_3$ is satisfied.

24. The power supply unit for the aerosol inhaler according to claim 7, wherein
the non-inversion input terminal of the operational amplifier is connected to the connection node of the first series circuit,
the inversion input terminal of the operational amplifier is connected to the connection node of the second series circuit,
the first element is connected to a low potential side of the load,
a negative default potential is input to a negative power supply terminal of the operational amplifier, or a circuit configured to subtract the default potential from a potential of the connection node which is electrically connected to the inversion input terminal of the operational amplifier in the second series circuit is provided, and
when the first electric resistance value is represented by $R_1$, the second electric resistance value is represented by $R_2$, the third electric resistance value is represented by $R_3$, the electric resistance value of the load is represented by $R_{HTR}$, a voltage applied to the first series circuit and the second series circuit is represented by $V_{OUT}$, and the default potential is represented by $V_{PSEUDO}$, $$R_1 \geq \frac{(V_{OUT} - V_{PSEUDO}) \cdot R_3 - V_{PSEDUDO} \cdot R_2}{(V_{OUT} + V_{PSEUDO}) \cdot R_2 + V_{PSEDUDO} \cdot R_3} \cdot R_{HTR} \quad \text{(IX)}$$

the formula (IX) is satisfied.

25. The power supply unit for the aerosol inhaler according to claim 24, wherein $$R_3 < \frac{V_{OUT} + 2V_{PSEUDO}}{V_{OUT} - 2V_{PSEUDO}} \cdot R_2 \quad \text{(X)}$$

the formula (X) is satisfied.

26. The power supply unit for the aerosol inhaler according to claim 1, further comprising:
a control device configured to supply power to the first series circuit and the second series circuit such that the load generates aerosol from the aerosol generation source based on an aerosol generation request.

27. The power supply unit for the aerosol inhaler according to claim 26, wherein
the control device is configured to acquire the temperature of the load based on an output of the operational amplifier while supplying the power to the first series circuit and the second series circuit such that the load generates the aerosol from the aerosol generation source.

* * * * *